United States Patent [19]
Trent et al.

[11] Patent Number: 5,532,389
[45] Date of Patent: Jul. 2, 1996

[54] PROCESS FOR PREPARING ALKYLENE OXIDES

[75] Inventors: David L. Trent, Lake Jackson, Tex.;
George J. Quarderer, Midland, Mich.;
Kim G. Bargeron, Midland, Mich.;
Douglas C. Greminger, Midland, Mich.; David J. Koranek, Lake Jackson, Tex.; Erik J. Stewart, Brazoria, Tex.; Curtis N. Swisher, Lake Jackson, Tex.; Cheryl A. Tirtowidjojo, Lake Jackson, Tex.; Danil Tirtowidjojo, Lake Jackson, Tex.

[73] Assignee: The Dow Chemical Company, Midland, Mich.

[21] Appl. No.: 303,852

[22] Filed: Sep. 9, 1994

Related U.S. Application Data

[63] Continuation-in-part of Ser. No. 156,507, Nov. 23, 1993, abandoned.

[51] Int. Cl.⁶ .................... C07D 301/26; C07D 303/04; C07D 303/08; C07C 29/66
[52] U.S. Cl. ................. 549/522; 423/473; 423/474; 549/521; 568/847; 568/850
[58] Field of Search .................... 423/474, 473; 568/850, 847; 549/522, 521

[56] References Cited

U.S. PATENT DOCUMENTS

| | | |
|---|---|---|
| 975,613 | 11/1910 | Gartenmeister. |
| 1,308,796 | 7/1919 | McElroy. |
| 1,403,993 | 1/1922 | Wallace et al.. |
| 1,510,790 | 10/1924 | McElroy. |

(List continued on next page.)

FOREIGN PATENT DOCUMENTS

| | | | |
|---|---|---|---|
| 754531 | 8/1933 | France. | |
| 6917373 | 6/1970 | Netherlands | 568/847 |
| 799310 | 3/1982 | U.S.S.R.. | |
| 543944 | 3/1942 | United Kingdom. | |
| 1339650 | 12/1973 | United Kingdom. | |
| 1358839 | 7/1974 | United Kingdom. | |

OTHER PUBLICATIONS

Secoy et al., *This Journal*, "Solubility of Chlorine Monoxide in Water", vol. 63, pp. 2504–2508, (1941).
H. Imakawa, *Electrochemistry*, "Chemical Reactions . . . Aqueous Solution", vol. 18, pp. 382–385 (1950) translation.
H. Imakawa, *Electrochemistry*, "Studies on Chemical . . . Sodium Chlorate", vol. 19, pp. 271–274 (1951) translation.
Gleason et al., *J. Am. Chem. Soc.*, "Kinetics of the Chlorate–Sulfate Reaction", vol. 61, pp. 447–450, (1957).
Proceedings of the Fifth European/Second International Symposium on Chemical Reaction Engineering, B4, 1–7, Amsterdam 2, 3 & 4 (May 1972).

(List continued on next page.)

*Primary Examiner*—Joseph E. Evans

[57] ABSTRACT

A process of preparing alkylene oxides comprises steps of: (1) optionally forming a hypochlorite solution; (2) contacting chlorine with a solution of a hypochlorite below about 60° C., and a pH of less than about 5.5, with sufficient micromixing to achieve a product hypochlorous acid in a yield of at least about 80 percent; (3) separating at least a portion the hypochlorous acid from an aqueous metal chloride solution wherein the solution is sprayed as droplets; (4) distilling the remaining liquid phase; (5) absorbing the hypochlorous acid and dichlorine monoxide in low-chlorides water to produce a low-chlorides aqueous hypochlorous acid solution; (6) contacting the low-chlorides aqueous hypochlorous acid solution with an olefin in a continuous process to form a olefin chlorohydrin; (7) optionally contacting the olefin chlorohydrin with a base to form a alkylene oxide and a salt solution; and (8) optionally separating the alkylene oxide from the salt solution. (9) optionally removing chlorates from the chloride brine by contacting the chlorates with acid to convert the chlorates to chlorine; and (10) optionally recycling the chlorine. The process yields particularly high yields of the alkylene oxide without substantial production of by-products.

54 Claims, 5 Drawing Sheets

U.S. PATENT DOCUMENTS

| | | |
|---|---|---|
| 1,694,711 | 12/1928 | Levine . |
| 1,867,666 | 7/1932 | Henglein et al. . |
| 1,996,638 | 4/1935 | Britton et al. . |
| 2,007,168 | 7/1935 | Kautter . |
| 2,157,524 | 5/1939 | Cady . |
| 2,157,525 | 5/1939 | Cady . |
| 2,177,419 | 10/1939 | Engs et al. . |
| 2,240,344 | 4/1941 | Muskat et al. . |
| 2,272,818 | 2/1942 | Petroe . |
| 2,347,151 | 4/1944 | Crawford et al. . |
| 2,463,850 | 3/1949 | Brooks ................................. 549/522 |
| 3,133,877 | 5/1964 | Mixer . |
| 3,199,949 | 8/1965 | Clerbois et al. . |
| 3,247,227 | 4/1966 | White . |
| 3,261,874 | 7/1966 | Stogryn ................................. 549/522 |
| 3,282,966 | 11/1966 | Naugle, Jr. . |
| 3,285,976 | 11/1966 | Wegner et al. . |
| 3,477,205 | 11/1969 | Potop et al. . |
| 3,527,774 | 9/1970 | Rothe et al. . |
| 3,578,400 | 5/1971 | Wojtowicz et al. . |
| 3,598,874 | 8/1971 | Kloss et al. ............................ 568/850 |
| 3,616,385 | 10/1971 | Kloss et al. . |
| 3,718,598 | 2/1973 | Wojtowicz et al. . |
| 3,790,369 | 2/1974 | Olsson et al. . |
| 3,845,144 | 10/1974 | Bartholomé et al. . |
| 3,845,145 | 10/1974 | Wojtowicz et al. . |
| 3,886,187 | 5/1975 | Bartholomé et al. . |
| 3,925,540 | 12/1975 | Hatherly . |
| 4,017,592 | 4/1977 | Pénard et al. . |
| 4,059,421 | 11/1977 | Kurata et al. . |
| 4,146,578 | 3/1979 | Brennan et al. ........................ 423/473 |
| 4,147,761 | 4/1979 | Wojtowicz et al. . |
| 4,169,773 | 10/1979 | Lai et al. . |
| 4,240,885 | 12/1980 | Suciu et al. . |
| 4,243,492 | 1/1981 | Yamamura et al. . |
| 4,330,521 | 5/1982 | Glineur . |
| 4,348,372 | 9/1982 | Duncan et al. . |
| 4,415,460 | 11/1983 | Suciu et al. . |
| 4,481,088 | 11/1984 | Moore et al. . |
| 4,496,753 | 1/1985 | Kwon et al. ............................ 549/522 |
| 4,504,456 | 3/1985 | Yant et al. . |
| 4,584,178 | 4/1986 | Yant et al. . |
| 4,652,434 | 3/1987 | Bonsack et al. . |
| 4,744,956 | 5/1988 | Yant et al. . |
| 4,861,352 | 8/1989 | Cheng . |
| 4,869,785 | 9/1989 | Fasi et al. . |
| 5,037,627 | 8/1991 | Melton et al. . |
| 5,055,285 | 10/1991 | Duncan et al. . |
| 5,106,591 | 4/1992 | Hilliard et al. . |
| 5,116,593 | 5/1992 | Melton et al. . |
| 5,116,594 | 5/1992 | Hilliard et al. . |
| 5,146,011 | 9/1992 | Shen et al. . |
| 5,152,915 | 10/1992 | Ralston, Jr. et al. . |
| 5,194,238 | 3/1993 | Duncan et al. . |
| 5,213,771 | 5/1993 | Hilliard et al. . |
| 5,273,678 | 12/1993 | Deroux et al. . |

OTHER PUBLICATIONS

Levenspiel, O., *Chemical Reaction Engineering*, Second Edition, Ch. 9, "Nonideal Flow", John Wiley & Sons, Inc., New York (1972), pp. 253–271.

Kuchta et al., "Mechanical high–frequency dispersion equipment for laboratory and production", (1973).

Renard et al., *Laboratory Report 288*, "The Chemistry of Chlorine Monoxide", (1974).

Grünert et al., "Studies in Optimizing Production of Propylene Oxide by the Chlorohydrin Method", (1976).

K. H. Simmrock, *Hydrocarbon Processing*, "Compare Propylene Oxide Routes", pp. 105–113, (Nov. 1978).

Carra et al., *Chemical Engineering Science*, vol. 34, pp. 1123–1132, "Synthesis of Propylene Oxide from Propylene Chlorohydrins—I", (1979).

*Kirk–Othmer Encyclopedia of Chemical Technology*, Third Edition, vol. 5, pp. 848–864, "Chlorohydrins", (1979).

Knauth et al., *The Journal of Physical Chemistry*, vol. 83, No. 12, pp. 1604–1612, (1979).

*Kirk–Othmer Encyclopedia of Chemical Technology*, Third Edition, vol. 19, "Propylene Oxide", (1982).

Lahiri et al., *Chemical Engineering Science*, vol. 38, No. 7, pp. 1119–1133, (1983).

Y. T. Shah, *Advances in Chemical Engineering*, vol. 17, pp. 1–204, "Design Parameters for Mechanically Agitated Reactors", (1992).

Bikbulatov et al., New System of Hypochlorous Acid Preparation in Epichlorohydrin Production, 1984, vol. 4, pp. 201–202, CA: 100:212418A.

Bikbulatov et al., Chlorohydrins II, Preparation of a Stable Nonaqueous Sollution of Hypochlorous Acid, Izu, Sib. Otd. Akad, Nauk SSR, Ser. Khim Nauk, 1984, vol. 4, pp. 137–141, CA: 102:24092G.

International Search Report dated 31 Mar. 1995 issued by the EPO acting as the International Searching Authority in PCT/US94/13005.

PROCESS FOR PREPARING ALKYLENE OXIDES

This application is a continuation-in-part of the U.S. application Ser. No. 08/156,507, filed Nov. 23, 1993 and now abandoned which is incorporated herein in its entirety.

The present invention relates to production of alkylene oxides, particularly to processes of forming the oxides via the corresponding halohydrin (halohydrin processes).

Halohydrin processes for the production of alkylene oxides (epoxides) including ethylene oxide, propylene oxide, butylene oxide, epichlorohydrin, and the like advantageously involve the reaction of chlorine (or other halogen or hypohalite) with the corresponding olefin (ethylene, propylene, butene, allyl chloride, respectively) in aqueous solution to produce an intermediate halohydrin which is then reacted with a base to produce the desired epoxide and brine. The epoxide is advantageously stripped from the brine and is optionally separated from various by-products. The brine is optionally treated for removal of residual impurities. There are numerous variations on each of these reactions.

U.S. Pat. No. 3,282,966 (Nov. 1, 1966) (J. J. Naugle, Jr.), for example, describes a process for preparing propylene oxide by a chlorohydrin process. Naugle discloses mixing chlorine, propylene, and fresh water in a reactor to produce the intermediate propylene chlorohydrin in aqueous solution. This reaction is hereinafter referred to as hypochlorination. The chlorohydrin is then dehydrochlorinated to propylene oxide by reaction with a base such as calcium hydroxide. This reaction is also described by the terms epoxidation and saponification. S. Carra, et al., in "Synthesis of Propylene Oxide from Propylene Chlorohydrins—I: Kinetic Aspects of the Process", *Chemical Engineering Science*, vol. 34, pp. 1123–1132 (1979), also describes the use of sodium hydroxide for this reaction. Naugle then describes the stripping of the propylene oxide from the water in a distillation column as soon as possible to minimize hydration of the propylene oxide to propylene glycol. The bottoms fraction from this column contains calcium compounds, such as calcium chloride, a significant quantity of water and other impurities. The propylene oxide, containing some water, propylene dichloride and other impurities, are taken overhead for further purification through a series of distillation columns.

Richard O. Kirk and T. John Dempsey describe a similar process for propylene oxide in "Propylene Oxide", *Kirk-Othmer Encyclopedia of Chemical Technology*, third edition, vol. 19 (1982), pp. 246–274. The hypochlorination reaction (referred to as chlorohydrination in the report) involves sufficient water to reduce product propylene chlorohydrin (PCH) product concentration to 4–5.5 weight percent, which minimizes by-product propylene dichloride (PDC) formation to 4–8 percent loss of propylene and chlorine feed. PCH concentration is also kept low to minimize by-product ether formation. The reaction is carried out at 40°–90° C. with the exothermic reaction providing 10°–40° C. temperature rise depending on the water-to-chloride ratio. The epoxidation reaction is described as treatment of the chlorohydrin with aqueous base such as lime or caustic soda with approximately half the base used to neutralize the by-product hydrogen chloride and the balance used to convert the PCH to propylene oxide. About 10 mole percent excess alkalinity is used. The propylene oxide is then removed from the alkaline solution in a stripping column. The bottom stream of the stripping column contains 5–6 weight percent calcium chloride or 5–10 weight percent sodium chloride, several hundred parts per million (ppm) propylene glycol, and trace amounts of other organic compounds at a pH of about 11–12. Several methods for removal of organic contents, such as biological oxidation, are suggested. The overheads product of the stripping column containing the propylene oxide (about 26 weight percent), by-product organic compounds (about 4 weight percent), and water (about 70 weight percent) is sent to a series of distillation columns to purify the propylene oxide.

Such processes suffer from three major problems. The first is the production of by-product halogenated organic compounds, particularly di- and trihalides such as propylene dichloride (PDC) and trichloropropane (TCP) from the production of propylene oxide and epichlorohydrin, respectively. Formation of these by-products is related to the free halide ion concentration from the hydrolysis of halogen. Dilution with large volumes of water is frequently used to control halide ion concentration; however, dilution has practical and economic limits. Even with infinite dilution, these by-products are still formed (see Bartholome, E., et al, *Chem. React. Eng. Proc. Eur. Symp.*, 5th, 1972, B4, 1–7 (Eng). Elsevier: Amsterdam, Neth.) (U.K. Patent 1339650, Continuous Production of Propylene Chlorohydrin, 1973).

Some methods of overcoming production of chlorinated by-products result in formation of other by-products. For instance, Wojtowicz et al. in U.S. Pat. No. 3,845,145 (Oct. 29, 1974) describes carrying out the reaction of low chlorides hypochlorous acid (HOCl) with olefins in the presence of a water saturated organic solvent such as methyl ethyl ketone (MEK) to reduce the formation of by-products such as propylene dichloride. However, this process has two major disadvantages: First, the HOCl reacts with the organic solvent to produce undesirable by-products such as chlorinated ketones. Second, the presence of the organic solvent adds additional process steps and, therefore, additional difficulty and equipment to the manufacture of the chlorohydrin.

A second process for making chlorohydrins with reduced by-product formation from low-chlorides HOCl solutions improves upon the process disclosed in U.S. Pat. No. 3,845,145 by using aqueous solutions of HOCl, eliminating the need for an organic solvent. U.S. Pat. No. 5,146,011 (Sep. 8, 1992) (Shen et al.) describes a process of feeding an aqueous solution of at least 10 percent by weight of HOCl substantially free of chloride, chlorate, and alkali metal ions to a reactor charged with water and the olefin. The reaction is at temperatures from the freezing point of water up to about 55° C. Such a process has several disadvantages. First, the low reaction temperature requires use of heat exchange equipment to remove the heat of reaction. Second, Shen requires the use of high concentration (greater than 10 weight percent, preferably from about 20 to about 65, and most preferably from about 35 to about 55 percent by weight) HOCl solutions. In addition Shen suggests preferred use of a batchwise reactor.

Several processes are described in the art for producing a low chlorides aqueous solution of hypochlorous acid. Crawford et al. in U.S. Pat. No. 2,347,151 disclose a process of distilling hypochlorous acid solutions in the presence of halogen gas to achieve low concentrations of halide ion in an aqueous hypochlorous acid. In the process disclosed by Crawford, halide containing aqueous solutions of hypochlorous acid are preferably fed to an intermediate position of a distillation or stripping column countercurrent to a rising stream of steam and chlorine gas. The distillation of hypochlorous acid is generally effected at a temperature of about 100° C. at atmospheric pressure. Use of lower pressures will vary the degree of heating necessary for the distillation. Crawford does not discuss the effect of hypochlorous acid feed concentration on the recovered yield, but uses a maximum of about 0.5 molar feed concentration in his examples.

Wojtowicz et al. describes in U.S. Pat. No. 4,147,761 (Apr. 3, 1979) another process for producing hypochlorous acid solutions which involves passing chlorine gas over the surface of an alkali metal hydroxide solution (from about 10 to about 80 percent by weight) at a temperature from about 0° C. to about 50° C., preferably from about 5° C. to about 20° C. The reactor is equipped with a refrigeration means to control the temperature sufficiently low to minimize alkali metal hypochlorite product decomposition. The HOCl formed on the surface of the liquid is partially vaporized and removed with the gas and partially absorbed into the liquid to form hypochlorite. The HOCl in the vapor phase is absorbed into water to produce the hypochlorous acid solution. The liquid phase of the reactor is an aqueous slurry of alkali metal hypochlorite and alkali metal chloride.

Brennan et al. (U.S. Pat. No. 4,146,578; Mar. 27, 1979) Melton et al. (U.S. Pat. No. 5,037,627; Aug. 6, 1991), and Melton et al. (U.S. Pat. No. 5,116,593; May 26, 1992) disclose methods for preparation of low chloride aqueous HOCl solutions. Each of the processes described in these patents involves spraying aqueous solutions of metal hydroxides into fine droplets into a chlorine atmosphere to react with chlorine gas to produce the HOCl vapor and a residue that contains solid metal chlorides, such as sodium chloride. The processes described by these patents have the disadvantage that energy is required to remove (dry) the water from the product metal chloride salt. Additionally, solid metal chlorides salts are difficult to handle, requiring special solids handling equipment (such as that described in U.S. Pat. No. 5,116,594 and 5,106,591), and present a waste disposal problem.

A second problem with existing chlorohydrin alkylene oxide technology involves treating and disposing of the volume of water frequently used to dilute reactants. Production of one kilogram (kg) of product propylene oxide often results in greater than 40 kg of water containing 5–10 weight percent sodium chloride salt or 5–6 weight percent calcium chloride salt. These dilution levels render this water of little or no commercial value. It must, therefore, be discharged after suitable treatment. (K. H. Simmrock, "Compare Propylene Oxide Routes", *Hydrocarbon Processing*, vol. 57, Nov. 1978, pp. 109–110.)

The third problem with existing chlorohydrin alkylene oxide technology is that the waste water (brine) must be treated for removal of organic compounds (primarily by-products) prior to discharge. The brine often contains halogenated organic compounds not completely removed with the chlorohydrin and generally contains polyhydric alcohols such as glycol or glycerol. More polyhydric alcohols are generally produced when a weaker base like lime rather than a stronger base like sodium hydroxide (caustic) is used to generate an epoxide from the chlorohydrin. Lime is typically used, however, because it is a more readily available and cheaper raw material.

SUMMARY OF THE INVENTION

The invention includes a, preferably continuous, process comprising steps of:

(1) Optionally contacting metal hydroxide or oxide with chlorine to form a metal hypochlorite solution;

(2) Contacting chlorine with a solution of a metal hypochlorite at a temperature below about 60° C., and a pH of less than about 5.5, with sufficient micromixing to achieve a product hypochlorous acid in a yield of at least about 80 mole percent based on hypochlorite in an aqueous metal chloride solution;

(3) Separating at least a portion of the hypochlorous acid from the aqueous metal chloride solution thereof, hereinafter referred to as chloride brine, wherein the solution is sprayed as droplets having a volume median diameter of less than about 500 micrometers into a vapor stream such that at least about 30 mole percent of the hypochlorous acid is desorbed from a liquid phase into a vapor phase where hypochlorous acid and dichlorine monoxide are in equilibrium;

(4) Distilling the remaining liquid phase to obtain additional hypochlorous acid and dichlorine monoxide vapor;

(5) Absorbing the hypochlorous acid and dichlorine monoxide in low-chlorides water to produce a low-chlorides aqueous hypochlorous acid solution;

(6) Contacting the low-chlorides aqueous hypochlorous acid solution with an olefin in a continuous process using a continuous stirred tank reactor to maintain a uniform steady-state HOCl concentration in the reactor of 0.2 weight percent or less to form a corresponding olefin chlorohydrin;

(7) Optionally contacting the olefin chlorohydrin with a base to form a corresponding alkylene oxide and a salt solution; and (8) Optionally separating the alkylene oxide from the salt solution.

(9) Optionally removing chlorates from the chloride brine from at least one of Steps 3 or 4 by contacting the chlorates with acid to convert the chlorates to chlorine; and

(10) Optionally recycling the chlorine to at least one of Steps 1 or 4.

The process also includes several of the steps taken independently of the overall process. Thus, one aspect of the invention is a process for the manufacture of hypochlorous acid comprising a step of contacting chlorine and a solution of a metal hypochlorite having a hypochlorite ion concentration of at least about 1 mole/liter (1M) at a temperature below about 60° C., and a pH of less than about 5.5, with sufficient micromixing to achieve a product hypochlorous acid in a yield of at least about 80 percent based on hypochlorite with less than about a 20 percent yield of chlorate. Another aspect of the invention is a process for the manufacture of hypochlorous acid comprising a step of separating the hypochlorous acid from an aqueous metal chloride solution thereof, hereinafter referred to as chloride brine, by first spraying the liquid into a chlorine-containing vapor stream with subsequent distillation of the liquid. The solution is sprayed as droplets having a volume median diameter of less than about 500 micrometers into a vapor stream containing chlorine, water vapor, and air such that at least about 30 mole percent of the hypochlorous acid is desorbed from the liquid into the vapor phase as hypochlorous acid and dichlorine monoxide as a result of the spray atomization, followed by further stripping of HOCl from the liquid phase into a vapor phase by distillation. The HOCl and dichlorine monoxide are recovered from the vapor phase by absorption in low-chlorides water in a separate device to provide a solution of low-chlorides HOCl in a concentration of less than 7 weight percent. Yet another aspect of the invention is a process of preparing a corresponding olefin chlorohydrin comprising a step of contacting a low-chlorides aqueous hypochlorous acid solution having a hypochlorous acid concentration of less than about 7 weight percent with an olefin in a continuous process using a continuous stirred tank reactor at a temperature of at least about 60° C., pressure greater than one atmosphere (101.3 kPa), less than 30 minutes residence time, with internal gas recycle, and backmix stirring sufficient to maintain a uniform steady-state HOCl concentration in the reactor at about 0.2 weight percent or less to form a corresponding olefin chlorohydrin, while minimizing formation of chlorinated ketones. The 0.2 weight percent or less HOCl concentration in the reactor is kept uniform by proper mixing in the reactor, and is kept low by a combination of dilution of the feed HOCl with the reactor contents and of reaction kinetics.

The overall process advantageously provides a method to reduce by-product halogenated organic compounds, preferably by at least about half as compared with, e.g. propylene dichloride (PDC) formation from reaction of gaseous propylene with gaseous chlorine in the presence of water in a continuous reactor. Advantageously, the process reduces the water needed for the chlorohydrin reaction, especially when hypochlorous acid reactant is used at a concentration of greater than about 3 percent by weight in Step 6 and no additional water dilution is used.

In comparison to the high concentrations of hydroxide solutions (for example, 50 weight percent sodium hydroxide) used in the teachings of Brennan et al. (U.S. Pat. No. 4,146,578), Wojtowicz et al. (U.S. Pat. No. 4,147,761), and Melton et al. (U.S. Pat. No. 5,037,627), the present invention in a preferred embodiment involves use of more readily available alkaline earth hydroxide aqueous slurries of lower concentration, such as 15 weight percent calcium hydroxide, to react with the chlorine to produce HOCl with a residue after distillation of an aqueous solution of, for example, calcium chloride—i.e., no solid residue to handle. In another embodiment, the present invention uses low concentrations of sodium hydroxide such as that produced in a diaphragm electrolytic cell (8–12 weight percent sodium hydroxide), hence additional equipment and energy are not required to concentrate the sodium hydroxide and no solid residue handling is required. These advantages of use of lower concentration raw materials and no solid product handling are gained by conducting the reaction chemistry external to the HOCl separation device. The reactor/separator devices of Brennan et al. and Melton et al. require spraying the feed hydroxide liquor in a mist that makes the use of alkaline earth hydroxide slurries more difficult. The process taught by Wojtowicz et al., while allowing easier use of slurry reactants, suffers from poor HOCl selectivities, as shown in the examples, of about 40 mole percent, because hypochlorite product is left in the salt slurry from which the HOCl is removed and about a 20 mole percent selectivity of chlorates indicates additional loss of hypochlorite. We have found that the use of a spray atomization means to produce small (less than about 500 micrometers) droplets of hypochlorous acid solution coupled with distillation advantageously improves the recovery of hypochlorous acid to as high as 95 percent of the starting hypochlorous acid.

In the epoxidation of chlorohydrin to epoxide (Step 7), it should be noted that a principle advantage of this invention is that the hydrochloric acid normally produced by the process of hypochlorination described by Naugle in U.S. Pat. No. 3,282,966 or by Kirk in "Propylene Oxide", *Kirk-Othmer Encyclopedia of Chemical Technology*, vol. 19, pp. 246–274, is absent in this invention (see Step 6). Therefore, additional caustic or lime is not required to neutralize the acid in the epoxidation reactor. In addition, the acid-catalyzed reaction of propylene oxide to propylene glycol that results from poor mixing of the base and chlorohydrin streams is eliminated, thus reducing the amount of glycol by-product produced during this epoxidation step (Step 7). See Wolfgang Grunert and Gerhard Just, "Studies in Optimizing Production of Propylene Oxide by the Chlorohydrin Method", *Wiss. Z. TH Leuna-Merseburg*, 18(3), 339–345, 1976, for data on reaction kinetics of the hydrolysis of propylene oxide to propylene glycol.

Yet another feature that distinguishes this invention from the art is the higher concentration (about 6.5–8.5 weight percent as compared with 4–5.5 weight percent) of chlorohydrin (e.g. propylene chlorohydrin, PCH) in the feed to the epoxidation reactor (see Kirk-Othmer, vol. 19, p. 254). Since the reaction rate of PCH and hydroxide is proportional to PCH concentration (see Carra, et at., "Synthesis of Propylene Oxide from Propylene Chlorohydrins—I: Kinetic Aspects of the Process", *Chemical Engineering Series*, vol. 34, pp. 1123–1132, 1979), less reaction time is needed to complete the reaction, resulting in smaller processing equipment.

The use of higher concentrations of propylene chlorohydrin in producing the propylene oxide (Step 7) which is permitted by the use of low-chlorides HOCl solutions in the reaction with propylene (Step 6) requires only 50–65 percent of the steam (or 0.5–1.3 kg steam per kg of propylene oxide produced) for stripping the propylene oxide as disclosed for instance by Bartholome et al. in U.S. Pat. No. 3,886,187. In addition the higher concentrations of 6.5–8.5 weight percent propylene chlorohydrin in the feed result in lower liquid flow rates and, coupled with the lower steam rates, means the equipment required is smaller than that described in the art.

DETAILED DESCRIPTION OF THE INVENTION

Figure 1:
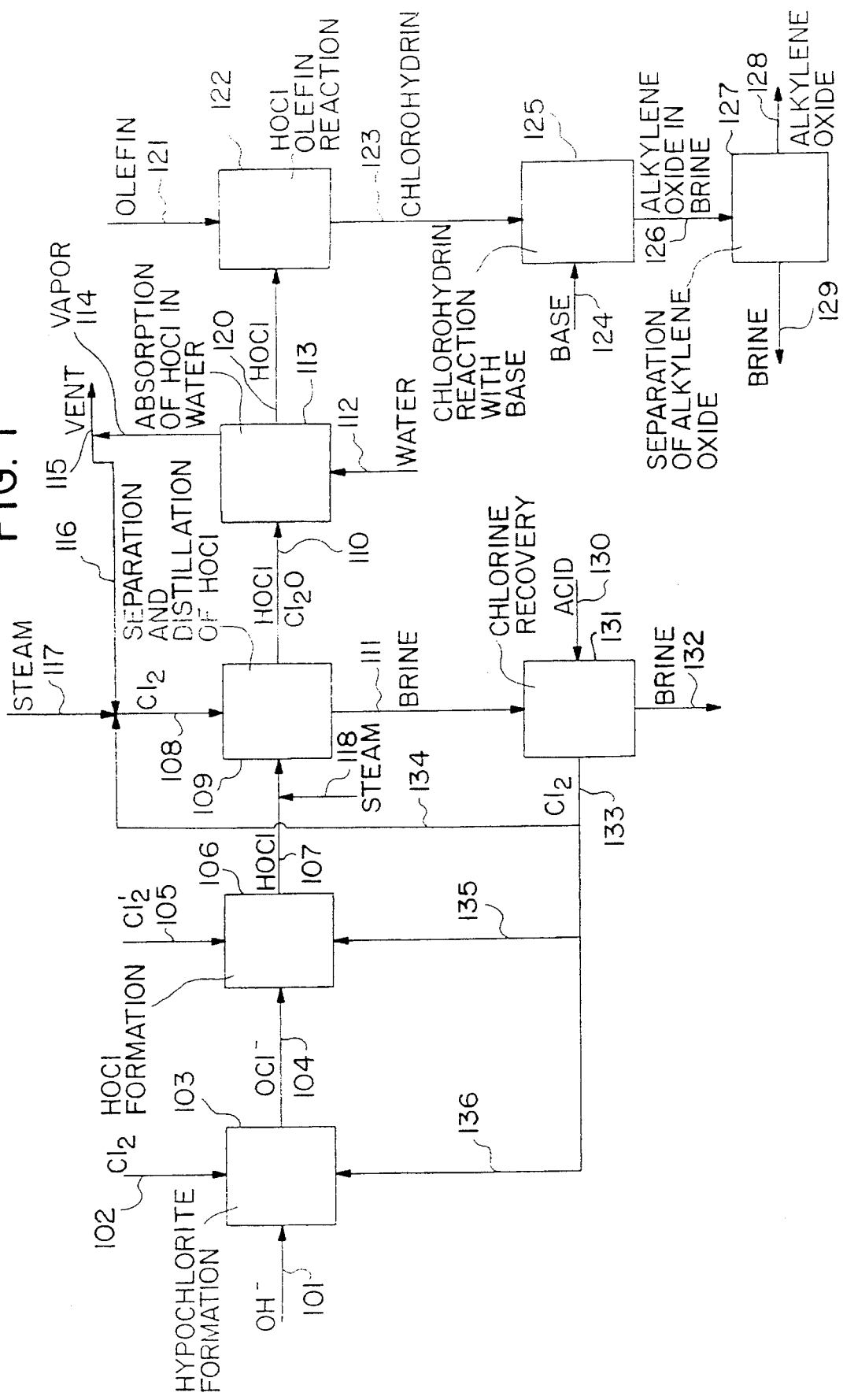
FIG. 1 is a schematic block flow diagram of one embodiment of the invention.

FIG. 1 is a block flow diagram illustrating a preferred embodiment of the process of this invention. Hydroxide in aqueous solution or slurry is supplied through line 101 and chlorine is supplied in line 102 to react in hypochlorite formation represented by box 103. The resulting aqueous hypochlorite solution is supplied through line 104 and chlorine through line 105 to HOCl (hypochlorous acid) formation represented in box 106. The HOCl is in aqueous solution and goes through line 107 to be joined by chlorine and steam from line 108 into separation and distillation of HOCl represented in box 109 from which brine exits through line 111. Steam enters through line 117 and combines in line 108 with chlorine from line 116 and line 134. Steam optionally enters line 118 when used to spray atomize the HOCl solution of line 107 in separation and distillation box 109. Vaporous HOCl and dichlorine monoxide ($Cl_2O$) leave separation and distillation box 109 through line 110 to be absorbed by water entering through line 112 in absorption of HOCl in water represented by box 113 from which unabsorbed vapor containing chlorine, water vapor and other materials inert to chlorine and HOCl exit through line 114 which is divided into a vent line 115 and, in this preferred embodiment, a recycle line 116 which joins line 108. Product aqueous HOCl exits box 113 through line 120, which with olefin, which enters through line 121, reacts in an HOCl olefin reaction represented by box 122 from which product chlorohydrin exits through line 123. Chlorohydrin from line 123 and base from line 124 go into a chlorohydrin reaction with base represented by box 125. The alkylene oxide product exits box 125 through line 126 to separation of alkylene oxide represented by box 127 from which purified alkylene oxide exits through line 128 and the brine from which the alkylene oxide is separated exits through line 129. In this preferred embodiment, brine in line 111 containing chlorates and acid (through line 130) are reacted for chlorine recovery represented by box 131 from which brine containing reduced chlorates exits through line 132 and chlorine exits through line 133 from which the chlorine enters hypochlorite formation box 103 through line 136, HOCl formation box 106 through line 135 or separation and distillation of HOCl box 109 via line 134 which joins line 108 through which other chlorine enters box 109.

Figure 2:
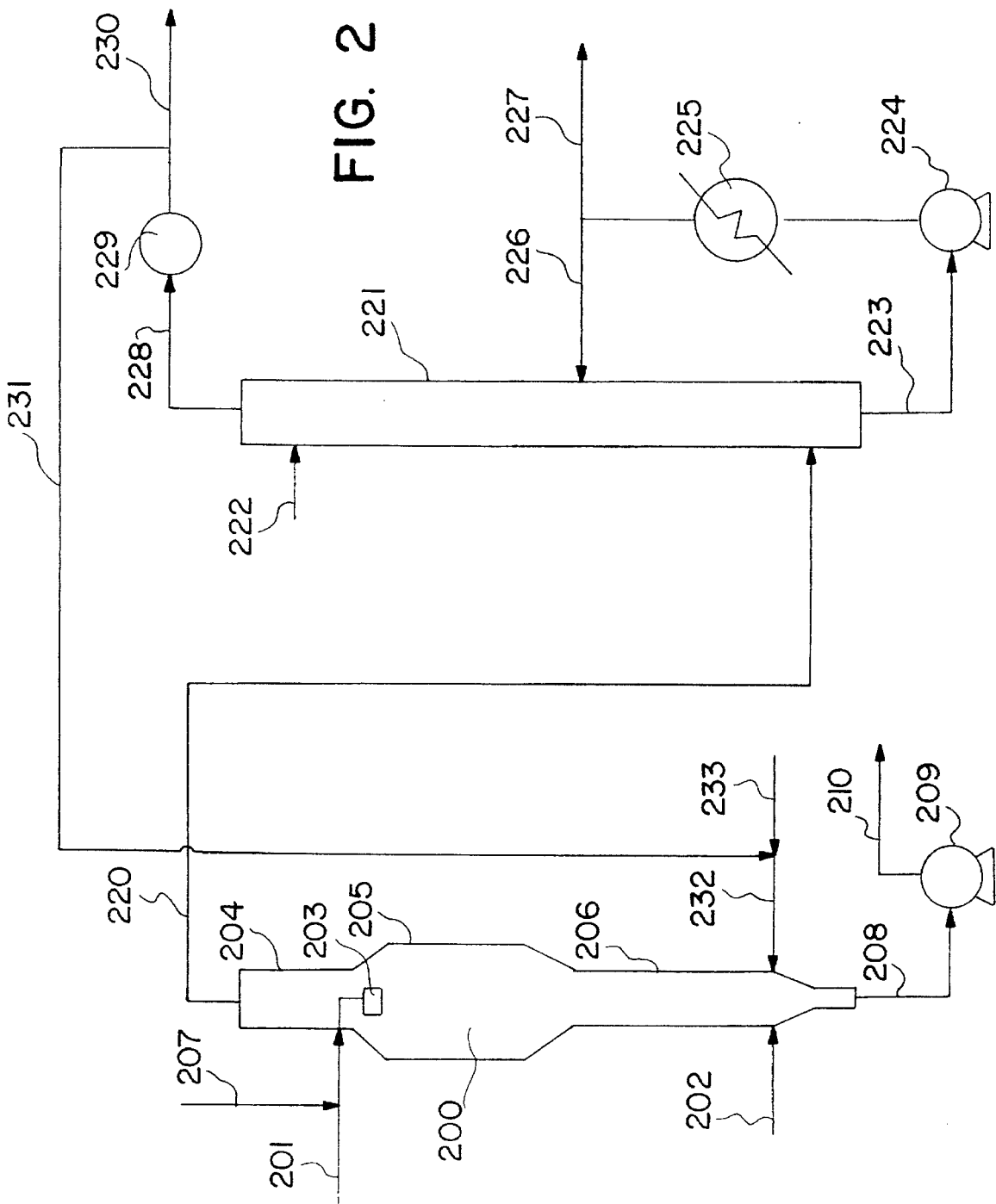
FIG. 2 is a diagrammatic representation of another embodiment of the invention.
Figure 3:
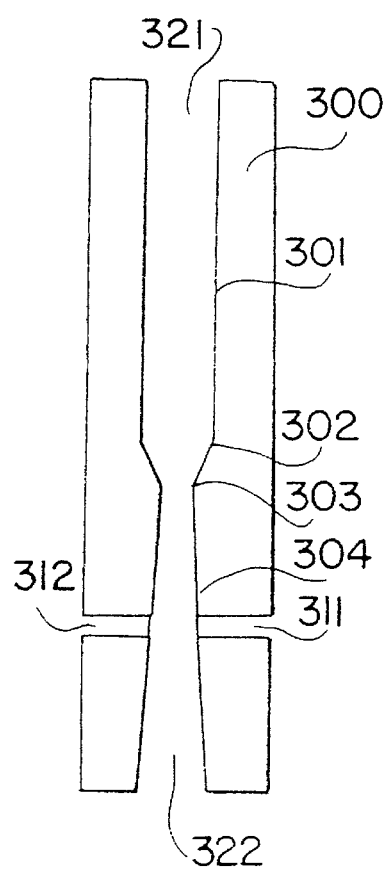
FIG. 3 represents a sectional view of one embodiment of a nozzle for spraying a solution of hypochlorous acid droplets.

In FIG. 2, an aqueous solution of HOCl enters stripper 200 through line 201 and spray means 203, which optionally uses steam from line 207, from which droplets of the solution enter upper open section 205 of stripper 200. HOCl is vaporized and goes into headspace 204 and out line 220; while liquid falls to distillation section 206 which is preferably packed, for further vaporization of HOCl. Stripping gas, including chlorine, enters through line 202 while steam enters through line 232 via line 233. Line 232 also contains recycled chlorine. Liquid remaining after stripping and distillation exits line 208 through pump 209 and out line 210. The vapor proceeds through line 220 to absorber 221 where it flows upward against a counter current of water which enters at line 222. Product HOCl solution exits line 223 through pump 224 through heat exchanger 225 from which a portion is recycled through line 226 while the remainder exits through line 227. Remaining vapor exits through line 228 and through blower 229 from which a portion exits through line 230 while a portion is recycled through line 231 back through line 232 to join incoming steam which enters through line 233.

Each step of the invention is explained beginning with chemical reactions illustrating the step with the use of chlorine as halogen and propylene as olefin. The invention includes the use of bases, such as sodium hydroxide, calcium hydroxide, magnesium hydroxide, calcium oxide, magnesium oxide or mixtures thereof, halogens including, and preferably, chlorine; and unsubstituted or inertly substituted olefins having from about 2 to about 10 carbon atoms. In each case, the olefin determines the halohydrin and epoxide. For instance when propylene is the olefin and chlorine is the halogen, the halohydrin is 1-chloro-2-propanol (also 2-chloropropanol) and the epoxide is 1,2-propylene oxide.

Although presented in steps, the invention is preferably a continuous process because a continuous process allows for use of a minimum amount of equipment to produce a maximum amount of product. This preference contrasts to the preference for batch operation in other processes involving producing chlorohydrins such as that disclosed by Shen et al. in U.S. Pat. No. 5,146,011.

1) Optionally contacting a metal hydroxide or oxide with chlorine to form a metal hypochlorite solution;

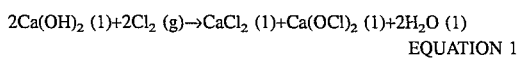
EQUATION 1

Chlorination (illustrative of halogenation) of aqueous solutions or slurries of metal hydroxides or oxides takes place by any process within the skill in the art which allows contact of the gaseous chlorine with the metal hydroxides. Agitation or stirring is advantageous to maintain contact. The reactor advantageously is a stirred tank reactor with mechanical agitation or a plug flow reactor with static mixing elements. In one preferred embodiment of the invention a reactor design includes a vessel with about one minute residence time, a pump for recirculation at a turnover rate of about 4 times per minute with fresh feed of chlorine and lime slurry to the suction of the pump, and a heat exchanger in the recycle loop to control temperature. Such a reactor design provides sufficient agitation within the pump and turbulence in the piping to mix the reactants, disperse the chlorine gas, and maintain the solids in solution until complete reaction is accomplished. Any reactor which provides such agitation is advantageously used.

An alkaline earth metal hydroxide is preferably used because of its ready availability and its low energy requirements compared to producing high concentrations of alkali metal hydroxides (for example 50 weight percent sodium hydroxide). Alkaline earth metal hydroxides are conveniently derived from the metal oxides such as calcium oxide, magnesium oxide, or mixtures thereof by reaction with water. Although alkaline earth metal hydroxides are preferred, alkali metal hydroxides are optionally used in this process as are mixtures of the alkaline earth metal hydroxides and alkali metal hydroxides.

The alkaline earth metal hydroxide is commercially available or is prepared by means within the skill in the art such as mixing an oxide such as lime with sufficient additional water to result in a calcium hydroxide concentration of preferably about 15 weight percent (2 molar) or less to maintain calcium hypochlorite produced by subsequent chlorination of the slurry in solution, but at least about 3.5 weight percent (0.5 molar) to minimize the cost of stripping the HOCl from the solution in a later process step, by minimizing water. The calcium hydroxide slurry is more preferably from about 1 to about 2 molar and most preferably from about 1.5 to about 2 molar concentration because of the reduced size of equipment and reduced energy requirements with use of higher concentrations.

Chlorine is preferably used in an amount about stoichiometric with the hydroxide, that is from about 90 to about 110 mole percent of the hydroxide to react all of the hydroxide to hypochlorite. The reaction preferably uses about 95–105 mole percent stoichiometry and most preferably about 95–100 mole percent. Using insufficient chlorine results in unreacted calcium hydroxide which increases the risk of plugging equipment if it settles out of solution, or results in yield loss if collected on filters. Using excessive chlorine results in generation of hypochlorous acid (HOCl) which accelerates formation of undesirable calcium chlorate which, in turn, represents a yield loss. This reaction is controlled by pH measurement with the desired pH of about 9–12, preferably about 9–11, more preferably about 10–11. pH control advantageously is achieved by monitoring pH with a pH probe or multiple pH probes and adjusting chlorine flow to the reactor to maintain the desired pH level.

Conditions of chlorination are not critical, but preferably the temperature is at least about 10° C., below which solid chlorine hydrate forms, more preferably the temperature is at least about 40° C. because this is a practical temperature for use of cooling tower water for temperature control as opposed to refrigeration. Higher temperatures accelerate decomposition of HOCl to the undesirable chlorates which in turn require disposal or recovery. Therefore, the maximum temperature is preferably less than or equal to about 80° C. Any means of heat exchange within the skill in the art is advantageously used to maintain the desired temperature.

Pressure of the reaction is not critical, but the pressure is preferably low enough to maintain the chlorine in a gaseous state. Although liquid chlorine is optionally used, there is no process advantage in doing so; furthermore, chlorine liquefaction requires energy for compression or refrigeration. Conveniently, the pressure is atmospheric, more preferably the pressure is less than about 5 atmospheres (506.5 kPa) and equal to or greater than about one atmosphere (101.3 kPa) to insure that all of the chlorine gas goes into solution to react with the hydroxide.

The reaction time is preferably sufficiently long to complete the reaction of the chlorine gas with the hydroxide, preferably at least about 5 seconds, more preferably at least about 15 seconds. Excess reaction time is of no value or harm to this reaction, but only increases the size of the equipment. The reaction time corresponds to the residence time in the reaction vessel, any recycle pump and associated piping.

The discharge of the reactor advantageously is filtered to remove inert solids such as calcium carbonate and silicates. The product solution of calcium hypochlorite and calcium chloride is a clear liquid that may have a slight pink to reddish color.

2) Contacting chlorine with a solution of a metal hypohalite at a temperature below about 60° C., and a pH of less than about 5.5, with sufficient micromixing to achieve a product hypochlorous acid (HOCl) in a yield of at least about 80 percent based on hypochlorite in an aqueous metal chloride solution;

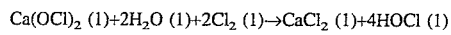

EQUATION 2

The main side reaction is chlorate formation:

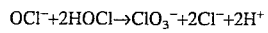

EQUATION 3

The rate at which this main side reaction occurs has been studied and reported by many authors (e.g., Kokoulina, D. V., and L. I. Krishtalik, "The Volume Reaction Forming Sodium Chlorate in the Anolyte of the Chlorate Electrolyzer", *Elektrokhymiyia*, vol. 7, No. 3, pp. 346–52, Mar. 1971). These studies show chlorate formation to be a function of HOCl concentration and hypochlorite concentration as shown in Equation 3. Kokoulina also showed this chlorate formation rate to be a maximum at pH values between 6 and 7 and to increase with temperature. To maximize the desired reaction and minimize the side reaction, the temperature is preferably kept low (less than about 60° C.), the HOCl concentration kept low (e.g. less than about 6 molar), and chlorine is in excess of stoichiometric to keep the pH low (less than about pH 5.5) (using e.g. greater than about 1 mole percent excess chlorine). At a pH of less than about 5.5, hypochlorite concentration approaches zero; and consequently, little chlorate is formed. Therefore, in the practice of the invention, the pH is preferably kept below about 5.5, more preferably less than about 4.5.

Conditions of chlorination are not critical, but to avoid excessive chlorate formation the temperature is preferably about 60° C. or less (above which temperature rapid decomposition of HOCl to chlorates is observed), more preferably about 45° C. or less. Preferably the temperature is at least about 10° C. at which temperature solid chlorine hydrate forms and precipitates. The preferred operating temperature is from about 20° C. to about 45° C. to avoid the need for use of refrigeration for cooling and to minimize formation of chlorates.

While either gaseous or liquid chlorine is suitably used in the practice of the invention, liquid chlorine is preferably used to speed the reaction rate between chlorine and hypochlorite. For this reason, the pressure is preferably sufficient to avoid gaseous chlorine, for example the pressure is at least about 100 psig (691 kPa gauge) at 25° C. and at least about 150 psig (1037 kPa gauge) at 40° C. These pressures represent the vapor pressure of chlorine at the respective temperatures. Presence of any other gases, such as air or nitrogen, raises the required pressure by the partial pressure of the additional gases.

While the amount of chlorine used is suitably any amount sufficient to react with the desired amount of calcium hypochlorite to form the HOCl, it is preferable to avoid having unused calcium hypochlorite because of the enhanced formation of chlorates in the presence of both HOCl and hypochlorite. Thus preferably at least an amount of chlorine stoichiometric to the amount of hypochlorite is used, more preferably an excess of chlorine is used to help lower the pH of the solution to avoid chlorate formation, more preferably the chlorine is used in an amount of from about 1 to about 20 mole percent excess over stoichiometric, most preferably from about 5 to about 10 mole percent excess.

Preferably, to minimize chlorate formation by achieving fast reaction times and achieving low pH quickly after the high pH hypochlorite solution and chlorine are combined, chlorination takes place in the presence of a high degree of agitation, that is sufficient agitation to achieve micromixing, that is mixing on a scale small enough that there are no localized areas of neutral pH where chlorate formation is accelerated. Micromixing is within the skill in the art as described by J. R. Bourne in "Mixing in Single-Phase Chemical Reactors", *Mixing in the Process Industries*, N. Harnby et al., ed., chapter. 10, 1985, pp. 170–184. The degree of micromixing required increases with increasing HOCl concentration. When the desired agitation is achieved, it is recognizable by at least about an 80 mole percent yield of hypochlorous acid accompanied by less than about 20 percent yield of chlorates. When there is less mixing, there are coexisting concentrations of hypochlorite and hypochlorous acid (HOCl) which result in formation of chlorate.

Figure 7:
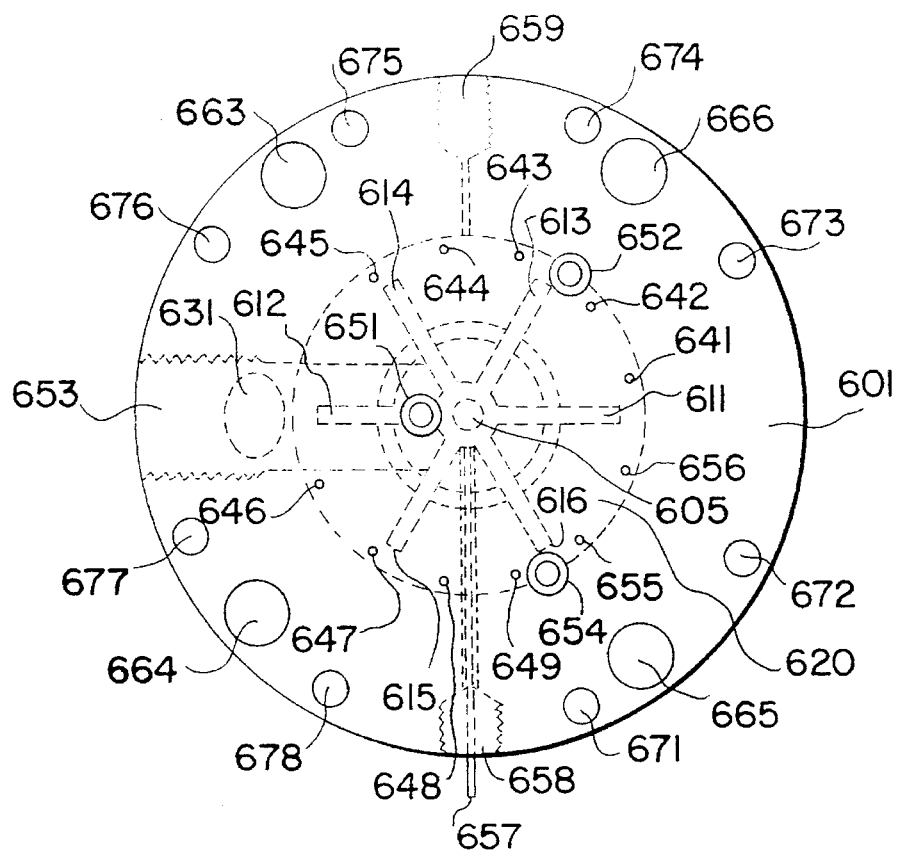
FIG. 7 represents an end view of the reactor represented in FIG. 6.
Figure 6:
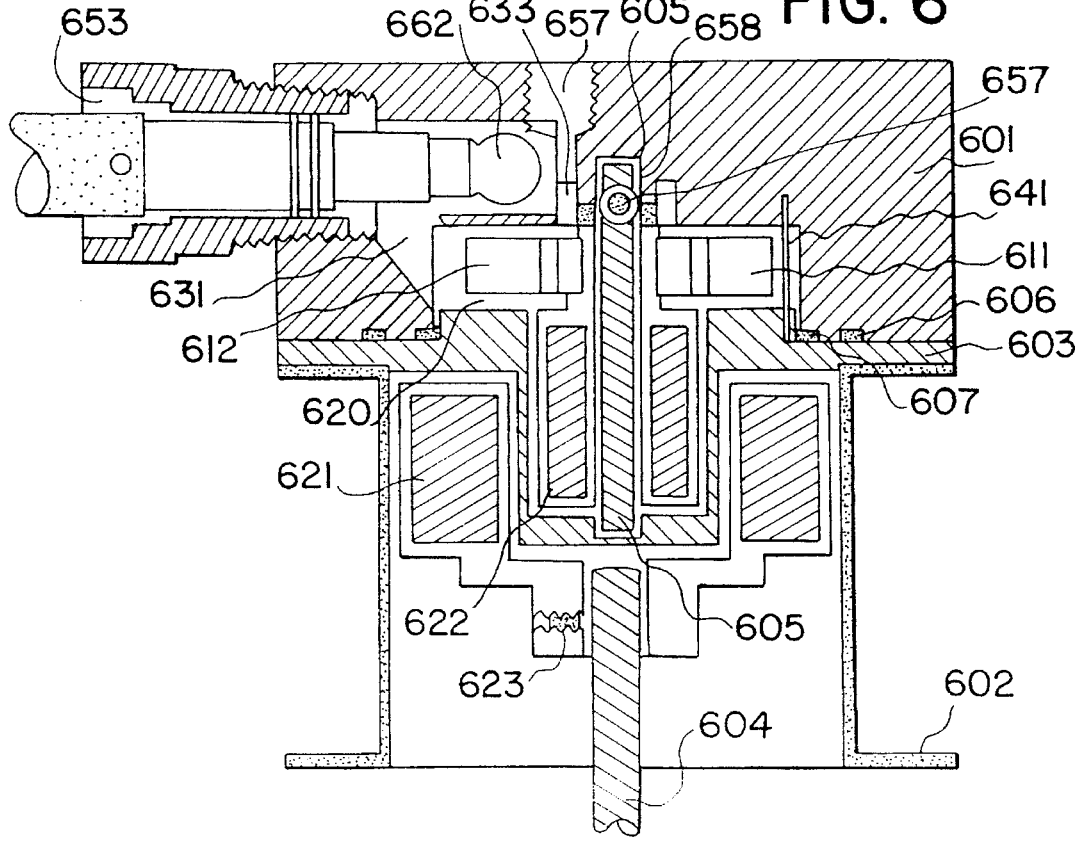
FIG. 6 represents a sectional view of one embodiment of a reactor for reacting hypochlorites with chlorine.

FIGS. 6 and 7 illustrate an embodiment of a reactor in which sufficient micromixing is attained. In FIG. 6, housing 601 is connected to a motor (not shown) through bracket 602. Bracket 602 is cylindrical in shape, completely surrounding motor shaft 604 and magnet 621, bolting on one end to a motor (not shown) and on the other end to housing 601. Through motor shaft 604, the motor turns magnet 621 inducing rotation of impeller magnet 622 which rotates impeller shaft 605, impeller blade 611 and impeller blade 612 inside reactor chamber 620. Set screw 623 attaches magnet 621 to motor shaft 604. O-ring 606 and o-ring 607 provide a seal between housing 601 and endplate 603 which in turn provides a seal from motor shaft 604 and magnet 621. Chlorine enters through tube 657 which passes concentrically through port 658 and discharges into reactor chamber 620 through recycle inlet 633 and reacts with hypochlorite which enters reactor chamber 620 through recycle inlet 633 from the annulus space between tube 657 and port 658. The hypochlorite, chlorine, and product HOCl solution are mixed in reactor chamber 620 where the reaction of hypochlorite and chlorine to HOCl occurs. Unreacted chlorine and product hypochlorous acid are circulated past pH probe 662 through internal recycle outlet 631 and returned to reactor chamber 620 through recycle inlet 633. Within reactor chamber 620 there are baffles illustrated by baffle 641. Thermocouple port 651 and pH probe 662 (through pH probe port 653) also enter reaction chamber 620. FIG. 7 shows the reactor from an end view. Thermocouple port 651, baffle 641, impeller 611, impeller 612, pH probe port 653, chlorine feed tube 657, hypochlorite feed port 658, and internal recycle outlet 631 are shown with reactor chamber 620 as in FIG. 6 for reference. Additionally there are impeller 613, impeller 614, impeller 615, and impeller 616 on impeller shaft 605. Baffle 642, baffle 643, baffle 644, baffle 645, baffle 646, baffle 647, baffle 648, baffle 649, baffle 655, and baffle 656 are also shown in FIG. 7. Pressure gauge port 659 allows measurement of pressure of reactor chamber 620 through use of a pressure gauge (not shown). Product port 654 exits reaction chamber 620 as does sample port 652. Heating liquid or cooling liquid enters inlet port 663 and exits outlet port 664; and enters port 665 and exits port 666. Bolts through bolt hole 671, bolt hole 672, bolt hole 673, bolt hole 674, bolt hole 675, bolt hole 676, bolt hole 677, and bolt hole 678 hold the housing 601 to endplate 603 and bracket 602.

The reaction is preferably carried out in a backmix reactor, that is a reactor which has exit product compositions and temperature equivalent to bulk compositions and temperature at any point within the reactor. An homogenizer that employs a rotor and stator for turbulence and an internal recycle to achieve the desired CSTR conditions is a preferred reactor. Devices, such as the Votator CR Mixer, are commercially available, for example, from Votator Division of Chemetron Corporation of Louisville, Ky., among others. Karlheinz Kuchta and Lothar F. Witt, Jr., describe the design and use of this type of mixer in "Mechanical High-frequency Dispersion Equipment for Laboratory and Production", *American Laboratory*, June, 1973, reprint. Decomposition of HOCl to chlorates is primarily a function of pH, with time and temperature being of secondary importance. Maximum decomposition rate occurs at about pH 7.2, with the rate approaching zero at pH greater than about 11 or pH less than about 4.5. Therefore, the product of this reactor preferably exits at pH less than about 4.5. Since the feed to the reactor is at about pH 11, the fresh feed is preferably mixed thoroughly and rapidly with the chlorine feed and the existing product in the reactor to avoid high decomposition rates in the intermediate pH range. Thus, it can be said that backmixing reduces chlorate formation.

The product of this step is hypochlorous acid (HOCl) in calcium chloride brine, preferably in 80 or greater percent yield, most preferably greater than 95 percent yield, based on the hypochlorite in the feed. As explained previously, the HOCl concentration is preferably kept low to minimize chlorate formation. Concentrations of less than about 6 moles/liter are considered low; the concentration is, however, more preferably less than about 4.5 moles/liter. These low concentrations are maintained by controlling the calcium hydroxide feed concentration to the first chlorination step (Step 1).

(3) Separating at least a portion of the hypochlorous acid from the aqueous metal chloride solution thereof (hereinafter referred to as chloride brine) wherein the solution is sprayed as droplets having a volume median diameter of less than about 500 micrometers into a vapor stream such that at least about 30 mole percent of the hypochlorous acid is desorbed from a liquid phase into a vapor phase where hypochlorous acid and dichlorine monoxide are in equilibrium with each other and (4) distilling the remaining liquid phase to obtain additional hypochlorous acid and dichlorine monoxide vapor;

The main reactions involve the conversion of aqueous HOCl to HOCl vapor and gaseous $Cl_2O$.

$$HOCl\ (l) \rightarrow HOCl\ (g) \qquad \text{EQUATION 4}$$

$$2\ HOCl\ (g) \rightarrow Cl_2O\ (g) + H_2O\ (g) \qquad \text{EQUATION 5}$$

The main side reaction is the decomposition of HOCl in the aqueous phase to chlorate as in the previous step. To minimize this side reaction residence times are advantageously kept low and a chlorine or other non-reacting gas, for instance nitrogen or steam, atmosphere is preferably maintained.

Another possible side reaction involves the explosive decomposition of dichlorine monoxide in the vapor space when concentrations exceed about 23 mole percent and an ignition source is present:

$$Cl_2O\ (g) \rightarrow Cl_2\ (g) + \tfrac{1}{2}\ O_2\ (g) \qquad \text{EQUATION 6}$$

Dilution with a non-reacting gas such as nitrogen, steam, or preferably chlorine, is effective in avoiding the explosive decomposition concentration of $Cl_2O$. Avoiding a source of ignition is also advantageous. The vapor pressure of $Cl_2O$ above water solutions dictates that an HOCl concentration of greater than about 4.5 molar is required for concentrations of $Cl_2O$ greater than 23 mole percent in the vapor phase.

The separation preferably takes place in a distillation column such that the separating and distilling steps are concurrent; the distillation column is also referred to herein as a stripping column or stripper, which is preferably at least partially packed. Although a trayed column is suitably used for the gas/liquid contacting for the stripping, packing is preferred due to its generally enhanced gas/liquid contacting and lower liquid hold up. The packing, in a preferred embodiment, is advantageously any commercially available material such as random packing (saddles, pall rings, and similar packings) or structured packing (Goodloe column packing, a wire mesh packing commercially available from Metex Corporation; Sulzer packing, a corrugated sheet packing commercially available from Koch Engineering Company, Inc.; and the like) and is preferably of a material resistant to corrosive chemicals, particularly HOCl and $Cl_2O$ (such as plastic, ceramic, titanium, and the like). The preferred packing material is that which achieves the maximum mass transfer with the minimum of liquid residence time such as structured packings. At least about 1 theoretical transfer unit in addition to the initial HOCl separation from the atomization nozzle section is preferred such that less than 1 percent of the initial HOCl remains in the brine solution that exits the bottom of the column.

The distillation column is preferably a stripping column, that is a stripping gas is introduced upward through the column countercurrent to the downward introduction of hypochlorous acid solution. This stripping gas provides most of the vapor stream into which the solution droplets are sprayed. The remaining vapor comes from evaporated water and HOCl. The stripping gas is preferably comprised of steam and chlorine, which are preferably introduced below the packing or trays. Steam introduced below the packing has two functions: to provide energy to vaporize the remaining HOCl and to provide the stripping gas for the required mass transfer. The steam advantageously is fresh steam or recycled steam, for instance from the top of an absorber column (Step 5) or from other parts of the process. When recycle gas from the absorber column (Step 5) is used as recycle steam, it should be noted that such gas contains chlorine gas and water vapor (steam) plus a small amount of inert compounds such as air from leaks in the equipment. The composition of the recycle gas is a function of the temperature and pressure of the absorber column (see discussion in Step 5 for preferred operating conditions). Sufficient fresh steam and recycle gas, containing water vapor and chlorine, are used to provide a stripping factor of about 1.0–3.0, preferably 1.1–1.5. Stripping factor is defined as the slope of the HOCl vapor/liquid equilibrium curve times the ratio of gas to liquid molar flow rates (Treybal, Robert E., *Mass-Transfer Operations, Second Edition,* 1968, pp. 111–112). A stripping factor of greater than about 3.0 provides little additional stripping, but requires larger equipment. Stripping factors below 1.0 will not allow complete stripping of the HOCl from the liquid. Sufficient chlorine is preferably used to maintain the liquid in the stripper at a pH of less than about 5.5, more preferably less than about 4.5. This amount corresponds to about 0.5–4 kg chlorine/kg steam, preferably 2 kg chlorine/kg steam. This chlorine advantageously is fresh gaseous chlorine or recycled chlorine, for instance from the top of an absorber column (Step 5) or from other parts of the process such as off-gas from the chlorate removal reactor (Step 9).

Although the preferred embodiment has a mixed steam and chlorine atmosphere, in the practice of the invention, either steam or chlorine alone, or even other gases inert to the reactants present are suitably used.

The HOCl in brine produced in Step 2 is advantageously injected into the column at a point above the trays or the packing. In a preferred embodiment, the HOCl and brine are sprayed or atomized, that is reduced to small droplets so that the HOCl is easily separated from the water. Any atomizing means within the skill in the art is suitably used. Preferably the volume median droplet size out of the atomizing means is less than about 500 micrometers, more preferably less than about 200 micrometers. The means used for atomization is preferably any spray nozzle within the skill in the art that achieves the preferred droplet size, more preferably one that operates on the principle of gas expansion to break up the liquid into fine droplets because this provides fast and efficient atomization or a single phase liquid spray nozzle.

In a preferred embodiment, the HOCl brine is injected along with steam through the same nozzle (two-phase mixing nozzle) to preheat the liquid to the desired temperature and to provide efficient atomization. More preferably, the steam provides sufficient heat to raise the temperature of the combined steam and brine to at least about 40° C., most preferably at least about 50° C.; more preferably the temperature is 100° C. or less, most preferably about 80° C. or less. Use of steam as an atomizing fluid has an advantage of resulting in a high rate of heating of the droplets such that they can be equilibrated into vapor and liquid before they contact vessel walls or packing. These temperatures are conveniently obtained using preferably at least about 0.1 kg steam/kg feed, more preferably at least about 0.2 kg steam/kg feed, and preferably less than about 1.0 kg steam/kg feed, more preferably about 0.5 kg steam/kg feed or less where kg feed is the weight of incoming aqueous HOCl in brine solution. Since the majority of the added steam ultimately results in diluting the brine, it is advantageous to minimize the amount of steam by using high pressure atomizing steam.

In a two-phase spray or atomization nozzle the gas is accelerated to sonic velocity in a Venturi. Liquid is mixed with the gas either before the gas is accelerated or just after. The large forces from the high acceleration break the liquid into fine droplets, advantageously with a very short (milliseconds) residence time in the nozzle. Atomization occurs in the mixing section of the nozzle, and deceleration of the spray occurs in the downstream diverging section. When steam is used as the motive fluid, simultaneous rapid heating to the nozzle exit conditions occurs.

FIGS. 3, 4, and 5 illustrate representative types of two phase nozzles useful in the practice of the invention. In FIG. 3, the nozzle comprises a housing 300 having steam inlet 321 and spray outlet 322. Inlet 321 has a generally cylindrical section 301, a converging cone 302, a throat 303 and an diverging cone 304. Cylindrical section 301 has a length to inside diameter ratio of about 6–10. Converging cone 302 has an included angle of a measure sufficiently small to avoid excessive pressure drop and turbulence prior to throat 303, for example about 30 degrees. Throat 303 has an inside diameter and a length such that the steam achieves sonic velocity prior to diverging cone 304. Diverging cone 304 has an included angle sufficiently small to avoid backmixing in diverging cone 304, for example less than about 15 degrees, and a length sufficient to reduce the pressure to that of a distillation column into which the nozzle sprays. A first liquid inlet 311 and a second liquid inlet 312 are bored into the housing in the diverging cone for introduction of hypochlorous acid solution. First liquid inlet 311 and second liquid inlet 312 intersect diverging cone 304 at about ⅕ the length of diverging cone 304 as measured from the outlet of throat 303 to spray outlet 322. The nozzle represented in FIG. 3 is of a type referred to in the art as a sonic nozzle.

The nozzle represented by FIG. 4 is of a type referred to in the art as gas assisted internal mix nozzle and has a housing 401 surrounding a first cylindrical chamber 402, second cylindrical chamber 403, steam inlet port 431, converging cone 411, a throat 412 and an diverging cone 413 forming a spray outlet 432. Cylindrical section 402 provides for insertion of liquid inlet tube 422 and a means to seal the tube 422 to nozzle housing 401. Cylindrical section 403 has an inside diameter and a length sufficient to provide sufficient steam flow to converging cone 411 without excessive pressure drop. Converging cone 411 has an included angle of about 90 degrees or less and a length sufficient to connect chamber 403 to throat 412. Throat 412 has a diameter and a length such that steam and liquid from chamber 403 achieves a velocity sufficient to atomize the liquid into drops with a volume mean diameter of less than about 500 micrometers, for example about sonic velocity. Diverging cone 413 has an included angle sufficiently small to avoid backmixing in diverging cone 413, for example less than about 15 degrees and a length sufficient to reduce the pressure to that of the a distillation column into which the nozzle sprays. Liquid inlet tube 422 has a liquid inlet port 423 located outside housing 401. Liquid inlet tube 422 extends inside and outside housing 401 concentric therewith for the full length of cylindrical section 402 and the full length of cylindrical chamber 403. The tube has an external end 423 outside of housing 401 and an externally tapered end 424 within the housing just above the converging cone 411; the externally tapered end 424 terminates in an opening 425 for liquid to enter converging cone 411. Steam enters cylindrical chamber 403 through inlet port 431.

Figure 5:
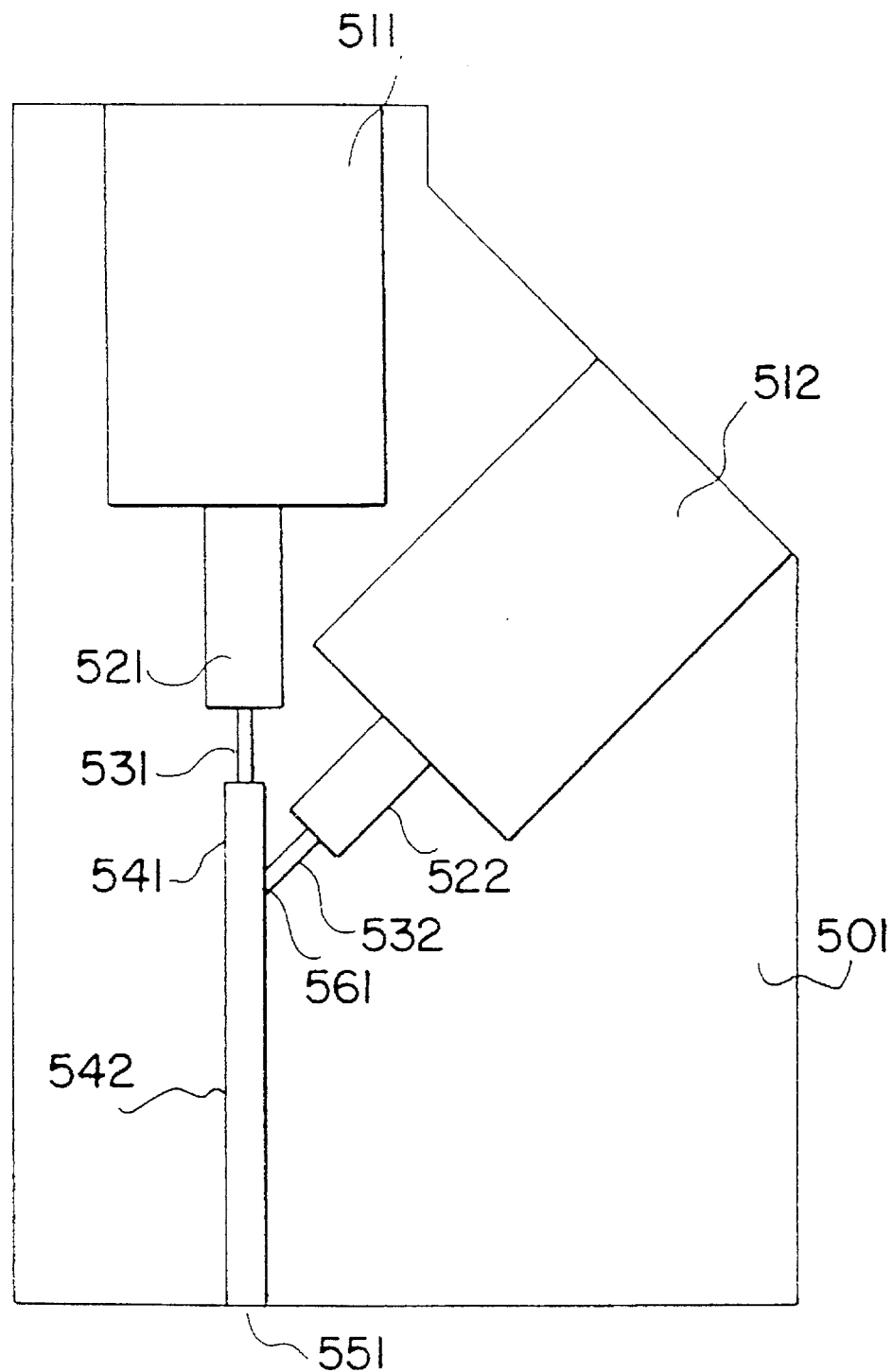
FIG. 5 represents a sectional view of yet another embodiment of a nozzle for spraying a solution of hypochlorous acid droplets.

The nozzle represented by FIG. 5 is of a type referred to in the art as a Y-jet nozzle and has a housing 501 with steam inlet port 511, liquid inlet port 512, steam connecting chamber 521, liquid connecting chamber 522, steam acceleration chamber 531, liquid acceleration chamber 532, steam expansion chamber 541, steam and liquid mixing chamber 542, and an outlet 551. Steam inlet port 511 allows connection of steam piping (not shown) to nozzle housing 501. Steam connecting chamber 521 is generally cylindrical with an inside diameter of about 4 times the inside diameter of steam acceleration chamber 531 and a length sufficient to connect steam port 511 to steam acceleration chamber 531. Steam acceleration chamber 531 is generally cylindrical with an inside diameter and a length such that the steam achieves sonic velocity prior to steam expansion chamber 541 with the steam flow rate limited to the minimum amount sufficient to achieve a volume median droplet size of less than about 500 micrometers from the discharge of outlet 551. Steam expansion chamber 541 has a length to diameter ratio of about 5 with a diameter equal to about 1–1.5 times the diameter of steam acceleration chamber 531. Steam and liquid mixing chamber 542 is an extension of steam expansion chamber 541 between outlet 551 and intersection 561 of steam expansion chamber 531 with liquid acceleration chamber 532. Steam and liquid mixing chamber 542 has the same diameter as steam expansion chamber 531 and a length to diameter ratio sufficient for uniform steam and liquid mixing and liquid droplet formation, for example about 12. Steam inlet port 511 is connected to steam connecting chamber 521, steam connecting chamber 521 to steam acceleration chamber 531, steam acceleration chamber 531 to steam expansion chamber 541, and steam expansion chamber 541 to steam and liquid mixing chamber 542 with center lines of each chamber being generally aligned. Liquid inlet port 512 allows connection of liquid feed piping (not shown) to nozzle housing 501. Liquid connecting chamber 522 is generally cylindrical with an inside diameter of about 4 times the inside diameter of liquid acceleration chamber 532 and a length sufficient to connect liquid inlet port 512 to liquid acceleration chamber 532. Liquid acceleration chamber 532 is generally cylindrical with a length to diameter ratio of about 5 and a length about equal to the length of steam acceleration chamber 531. Liquid inlet port 512 is connected to liquid connecting chamber 522, and liquid connecting chamber 522 to liquid acceleration chamber 532 with center lines of each chamber being generally aligned. Liquid acceleration chamber 532 and steam expansion chamber 541 intersect at an angle of about 45 degrees at intersection 561 where steam expansion chamber 541 joins steam and liquid mixing chamber 542.

Alternatively, a liquid spray nozzle is used without the steam to achieve the liquid droplet size at the exit of the nozzle. When a liquid spray nozzle is used, the liquid feed is preferably preheated before spraying or additional steam added to the stripper to heat the liquid spray inside the stripper. Single phase liquid spray nozzles designed to achieve volume median diameter drop sizes less than 500 micrometers are within the skill in the art and commercially available, for example from Spraying Systems Co.

One or more nozzles are used. A single atomization nozzle is mounted inside the stripping column preferably near the top of the column, more preferably above the trays or packing and along the centerline of the vessel. When multiple nozzles are used, they are oriented to provide uniform distribution of the liquid spray across the cross sectional area of the vessel without spraying liquid onto the walls of the vessel. The spray advantageously results in an equilibrium partitioning of HOCl between the vapor and liquid phases prior to entering the packing or trays for final stripping of the HOCl. Sufficient space is preferably provided between the exit of the nozzle and the packing or trays such that a velocity of the gas/liquid exiting the nozzle decelerates to near zero before contacting the packing. In addition, the nozzle is preferably designed with a full cone spray with cone angle of about 5–30 degrees, preferably about 15 degrees, and oriented such that the exit spray does not contact the walls of the column before contacting the packing. Because spraying to avoid wall contact often advantageously utilizes a larger diameter vessel than is preferred for the corresponding packed distillation column, the vessel for these steps, preferably has a larger diameter upper section for receiving spray than lower section for distillation. The shorter the time that the HOCl brine solution is maintained at higher temperatures before atomization is achieved, the higher the recoverable yield of HOCl because longer time would result in HOCl decomposition to chlorates.

Sufficient head space is preferably provided above the atomization nozzle to allow disengagement of entrained liquid droplets from the overheads vapor containing the HOCl and dichlorine monoxide along with chlorine and water vapor, that is the gas velocity, length of column, and droplet size are controlled to allow the liquid droplets to fall downward to the stripping section of the column. To aid this disengagement, the droplet size out of the nozzle is preferably greater than about 20 micrometers. Design parameters and requirements for preventing and/or eliminating entrained liquid drops from a gas are well known in the art and are described in many references, such as *Chemical Engineers' Handbook*, Fourth Edition, Robert H. Perry et al., ed., 1963, pp. 5–59 to 5–62 and 18–82 to 18–88. Liquid entrainment in the overheads gas is preferably minimized because the liquid contains salt which raises the chloride concentration of the absorbed HOCl in the next step (Step 5). Demisting devices are optionally and preferably used in the overheads vapor to remove entrained liquid drops from the gas. Such demisting devices include chevron horizontal demisters or vertical wire mesh demisters or others as described by Perry et al. Any liquid removed by the demister advantageously is returned to the bottom of the stripping column for discharge with the brine.

The length of the column, especially the distance between the nozzle outlet and packing is sufficient to provide at least 2 seconds of settling time for the liquid drops from the nozzle before contacting the column walls or the packing, but less than 120 seconds. This distance between the nozzle outlet and the packing is preferably sufficient to allow equilibration of the HOCl between the vapor and liquid phases but not great enough to permit decomposition of the HOCl remaining in the liquid before additional stripping can occur in the packed section of the column.

The amount of HOCl desorbed to the vapor space prior to the packed stripping section is preferably at least about 30 mole percent of the feed HOCl in the liquid. Higher desorption percentages are advantageous to minimize HOCl decomposition to chlorates. Temperature and HOCl feed concentrations above those preferred in the practice of the invention also increase the decomposition rate to chlorate, thus minimizing the overall recovery of HOCl from the spray atomization section and the stripping section. Thus, in balancing these considerations to maximize total HOCl recovery while minimizing chlorate formation one generally observes less than about 70 mole percent HOCl desorption before the liquid falls into the distillation section of the column.

While the pressure at which the distillation takes place is not critical, it is preferably sufficient pressure to provide sufficient temperature to partition the HOCl into gas and liquid phases (greater than about 50 mm Hg absolute (6.7 kPa) for greater than about 40° C.). Higher pressures of greater than about 1250 mm Hg (166.7 kPa) inhibit the amount of HOCl that partitions to the vapor phase from the liquid and can result in operating temperatures that provide too rapid decomposition of the HOCl to chlorates. Particularly in the preferred embodiment with the nozzle(s) or atomizing means, the column is preferably operated at about 50–1250 mm Hg (about 6.7–166.7 kPa) absolute pressure, more preferably about 300–1000 mm Hg (about 40–133.3 kPa), most preferably about 500–760 mm Hg (about 66.7–101.3 kPa).

In the practice of the invention according to the preferred embodiment which includes the nozzle(s) or atomizer means, a partitioning of HOCl into gaseous HOCl and $Cl_2O$ vapor and liquid aqueous HOCl solution advantageously occurs in the headspace of the stripper column which is operated at the preferred pressures. The mole percent of HOCl which partitions into the vapor phase in the head space is a function of feed concentration, temperature of entering hypochlorous acid solution, pressure, and the amount of vapor (chlorine, water, and inert compounds) present in the column. The vapor/liquid equilibrium data for HOCl partitioning between the liquid and vapor phases is well described in the literature, for example C. H. Secoy and G. H. Cady, "The Effect of Temperature and Pressure on the Solubility of Chlorine Monoxide in Water", *Journal of the American Chemical Society*, vol. 63, pp. 2504–8, (1941); H. Imagawa, "Chemical Reactions in the Chlorate Manufacturing Electrolytic Cell. Part 1: The Vapor Pressure of Hypochlorous Acid on its Aqueous Solution", *Journal of Electrochemical Society of Japan*, vol. 18, pp. 382–5, (1950); and H. Imagawa, "Studies on Chemical Reactions of the Chlorate Cell. Part 2: The Vapor Pressure of Hypochlorous Acid on its Mixed Aqueous Solution with Sodium Chlorate", *Journal of Electrochemical Society of Japan*, vol. 19, pp. 271–4, (1951). In addition the vapor phase equilibrium of HOCl and dichlorine monoxide is described by H. D. Knauth et al. in "Equilibrium Constant of the Gas Reaction $Cl_2O+H_2O=2HOCl$ and the Ultraviolet Spectrum of HOCl", *Journal of Physical Chemistry*, vol. 83, pp. 1604–1612, (1979). The range of HOCl desorption into the vapor space prior to the packed stripping section is about 30–70 mole percent of HOCl into vapor over the preferred ranges of variables.

The feed concentration is advantageously greater than about 0.5 molar HOCl, although lower concentrations are suitable. Concentrations of HOCl feed above about 4.5 molar, although possible, are undesirable when calcium or other alkaline earth metal compounds are used because of precipitation in calcium hypochlorite production (Step 1) and rapid decomposition rates of HOCl to chlorates. Preferred HOCl feed concentrations, therefore, are about 0.5–4.5 molar, more preferably about 2.0–4.0 molar.

The overhead vapor, which includes HOCl and $Cl_2O$, goes to produce a low chlorides aqueous solution of HOCl (Step 5) while the calcium chloride brine from the bottom of the distillation apparatus is optionally sent forward to brine treatment for chlorate removal (Step 9). A distillation apparatus designed and operated as described advantageously provides HOCl recovery yields based on the initial HOCl in the feed of greater than 80 mole percent.

5) Absorbing the HOCl and $Cl_2O$ in low-chlorides water to produce a low-chlorides aqueous solution of HOCl;

The reactions in this Step (5) are the inverse of those mentioned for the stripper (Steps 3 and 4) (Equations 4 and 5) with HOCl and $Cl_2O$ vapors being absorbed into water in this Step (5). Decomposition of HOCl to chlorate in the final HOCl solution is minimal because the HOCl solution is substantially free of chloride ions, that is preferably less than about 1000 ppm chlorides, more preferably less than about 500 ppm chlorides, and most preferably less than about 200 ppm chlorides. To produce a low chlorides HOCl solution substantially free of chloride ions, which is highly preferred in the practice of the invention, the water used for absorption is also very low in chloride concentration preferably less than about 1000 ppm, more preferably less than 500 ppm chlorides, and most preferably less than about 200 ppm and the liquid entrainment from the distillation step (Steps 3 and 4) is minimized as previously discussed.

To form the aqueous HOCl solution, HOCl and $Cl_2O$ vapor from the stripper are advantageously fed countercurrent to fresh (meaning water with low chlorides as defined) water in a spray, trayed or packed bed column (hereinafter absorber). The water enters the top of the absorber above the packing or trays, preferably at a temperature in the range of from about 10° C. to about 60° C., more preferably at about 40° C. The HOCl solution in the bottom of the column is preferably cooled by means within the skill in the art such as by use of a heat exchanger, to temperatures of from about 30° C. to about 60° C., preferably to about 40° C. This cooled HOCl solution is partially recycled to the column, preferably in the center portion of the column to help remove the heat of absorption of the HOCl and water vapor in order to maintain the column temperature below about 60° C., preferably below about 50° C. These temperatures are maintained to minimize the decomposition rate of HOCl to chlorates and to enhance the absorption of the HOCl into the water.

The absorber is advantageously a spray, packed bed or trayed column, preferably a packed bed column. The packing advantageously is a random packing such as pall rings or saddles or structured packing such as those described for the stripper in Step 4. The packing is preferably made of an advantageous corrosion resistant material such as ceramic, polytetrafluoroethylene polyvinylidene fluoride, or titanium. The packing is advantageously in at least two sections with liquid distributors on the top of each section to ensure the packing is fully wetted to provide optimum gas/liquid contacting. The top section distributes the fresh water into the column, while the bottom section distributes liquid from the top packed section and the recycle HOCl solution from the heat exchanger. Fresh water enters the top of the absorber, while gas from the stripper of Steps 3 and 4 enters below the bottom packed section. Liquid HOCl solution in the bottom of the column is cooled in an external heat exchanger and partially recycled to the column as described above. Uncondensed gases including, e.g. chlorine, water vapor, and inert materials such as air or nitrogen, exit the top of the absorber where it advantageously is partially recycled to the stripper of Steps 3 and 4 and partially removed for scrubbing to remove chlorine prior to venting to the atmosphere.

The column is preferably operated at about 50–1250 mm Hg (about 6.7–166.7 kPa) absolute pressure, more preferably about 300–1000 mm Hg (about 40–133.3 kPa), most preferably about 500–760 mm Hg (66.7–101.3 kPa). Discharge gases preferably are scrubbed e.g. with calcium hydroxide (lime) slurry or sodium hydroxide (caustic) or otherwise treated to remove any chlorine prior to venting. The scrubber liquid effluent, containing an aqueous mixture of metal hypochlorite, unreacted metal hydroxide, and metal chloride is optionally recycled to the first chlorination reaction (Step 1) for hypochlorite generation.

The product of this Step (5) is referred to herein as a "low chlorides" hypochlorous acid or HOCl solution and is preferably a solution of HOCl in water having a concentration of from about 1 to about 10 weight percent, more preferably from about 3 to about 7 weight percent HOCl, most preferably about 4–5 weight percent HOCl, preferably having less than about 1000 ppm chloride more preferably less than about 500 ppm chloride, most preferably less than about 200 ppm chloride at about 40°–60° C. Sufficient water is used to achieve these concentrations of HOCl. When the absorber column apparatus is as described for the preferred embodiment, the solution exits the bottom of the absorbing apparatus. The solution is fed forward to be reacted with olefin in Step 6. Chlorine and water vapor are preferably removed overhead from the absorber column and preferably are recycled to the HOCl stripper (Step 4) for instance via a mechanical blower or eductor. Alternatively, however, the water vapor and other materials are otherwise treated or recovered; for instance, the water vapor is optionally condensed, all by means within the skill in the art.

6) Contacting the low-chlorides aqueous hypochlorous acid solution with an olefin in a continuous process using a continuous stirred tank reactor with sufficient backmixing to maintain a uniform steady-state HOCl concentration in the reactor of about 0.2 weight percent or less to form a corresponding olefin chlorohydrin;

With propylene as the exemplary olefin, major reactions form propylene chlorohydrin, that is 1-chloro-2-propanol or 2-chloropropanol (PCH), propylene dichloride, that is 1,2-dichloropropane (PDC), dichloroisopropyl ether, that is bis-1-chloroisopropyl ether (DCIPE), dichlorohydrin, that is 1,3-dichloro-2-propanol or 2,3-dichloropropanol (DCH), and monochloroacetone, that is 1-chloropropanone (MCA) in reactions represented by the following:

| | |
|---|---|
| $Cl_2$ (g)→$Cl_2$ (l) | EQUATION 7 |
| HOCl (l)+HCl (l)→$Cl_2$ (l)+$H_2O$ (l) | EQUATION 8 |
| $C_3H_6$ (g)+$Cl_2$ (g)+$H_2O$ (l)→PCH (l)+HCl (l) | EQUATION 9 |
| $C_3H_6$ (g)+$Cl_2$ (g)→PDC (g) | EQUATION 10 |
| $C_3H_6$ (g)+PCH (l)+$Cl_2$ (g)→DCIPE (l)+HCl (l) | EQUATION 11 |
| $C_3H_6$+2 $Cl_2$+$H_2O$→DCH+2 HCl | EQUATION 12 |
| PCH+HOCl→MCA+$H_2O$+HCl | EQUATION 13 |

In Step (6) of contacting the low-chloride HOCl solution with an olefin to produce an alkene chlorohydrin in water, the incoming feed HOCl concentration is a concentration from about 1.0 to about 10 weight percent, preferably from about 3 to about 7 weight percent, more preferably from about 4 to about 5 weight percent because this provides a good balance between water requirements and by-product formation. A 5 weight percent HOCl solution for example represents about half the water normally used in this reaction by prior art processes such as that presented in "Propylene Oxide", *Kirk-Othmer Encyclopedia of Chemical Technology*, Third Edition, vol. 19 (1982), pp. 246–274. The low chlorides content of the HOCl solution results in less than 2 mole percent yield of propylene to PDC by-product formation compared to 4–8 mole percent yield of propylene to PDC in the prior art process presented in the reference. Use of higher concentrations of HOCl results in higher ether (DCIPE) by-product formation.

Any olefin, that is a compound having at least one carbon to carbon, non-aromatic, double bond, an alkene or arylalkene, is suitably used, preferably an olefin having from about 2 to about 10 carbon atoms, linear, branched or cyclic, preferably linear. Suitable olefins include amylenes, allene, butadiene, isoprene, allyl alcohol, cinnamyl alcohol, acrolein, mesityl oxide, allyl acetate, allyl ethers, vinyl chloride, allyl bromide, methallyl chloride, propylene, butylenes, ethylene, styrene and allyl chloride and their homologues and analogs. Propylene, butylene, ethylene, styrene and allyl chloride are the preferred olefins; with propylene, butylene, and allyl chloride more preferred and propylene most preferred. The olefin is unsubstituted (preferred) or inertly substituted, that is substituted with any group which does not undesirably interfere with formation of the chlorohydrin or the epoxide. Inert substitutents include chlorine, fluorine, phenyl and the like. The amount of olefin is advantageously at least about stoichiometric with the HOCl to insure complete reaction of the HOCl because unreacted HOCl often causes corrosion problems in downstream equipment. Preferably from about 0 to about 25 mole percent excess olefin, more preferably from about 1 to about 10 mole percent excess olefin is fed to the reactor.

Conditions of temperature, pressure and reaction times are not critical; any conditions under which the HOCl and olefin react are suitably used. The HOCl solution is advantageously fed to the reactor at a temperature of about 30–60° C. from Step 5, preferably about 40° C. Conveniently, the temperature of the olefin reaction is at least about 40° C. because lower temperatures require refrigeration or other cooling, more preferably the reaction temperature is at least about 60° C. If a reactor is run adiabatically, feed concentrations greater than about 3 percent, for example require some cooling to maintain temperature of about 70° C. or less. Preferably, the temperature is less than about 100° C., more preferably less than about 90° C., to avoid vaporization of the water and organic compounds in the reactor, and most preferably less than about 80° C. to avoid undesirable increases in by-product formation.

In the preferred embodiment, when a continuous stirred tank reactor (CSTR) is used, it operates isothermally, whereas a plug flow type reactor commonly operates adiabatically. The heat of reaction is, therefore, advantageously removed from a CSTR e.g. in a recycle heat exchanger and/or a reactor jacket. To minimize the external heating or cooling on the reactor, the heat of reaction is preferably matched with raw material feed temperatures such that the heat of reaction raises the feed temperatures to the desired reaction temperature. Matching the temperatures is within the skill in the art. For example a one molar HOCl feed concentration (about 5 weight percent HOCl) reacted with propylene adiabatically raises the temperature about 55° C. Therefore, if a reaction temperature of about 90° C. is desired, the feed temperature is advantageously about 35° C. A lesser spread between feed temperature and reaction temperature requires cooling, while a greater spread in temperatures requires heating. The temperature control is achieved by any means within the skill of the art, such as a jacketed reaction vessel, submersible coils in the reactor, or a heat exchanger in an external recycle line.

Conveniently, the pressure is at least about atmospheric, preferably at least about 2 atmospheres (202.6 kPa) gauge more preferably at least about 4 atmospheres (405.6 kPa) gauge, because the higher pressure enhances the mass transfer of the gaseous propylene, for example, with the HOCl solution, increasing the overall reaction rate. Conveniently, the pressure is less than about 150 psig (1037 kPa gauge), more preferably less than about 100 psig (691 kPa gauge), because the lower pressure requirements reduce the fabrication costs of the reactor.

Conveniently, the reaction time for propylene as example is at least about 5 minutes, more preferably at least about 10 minutes, because sufficient time is required for reaction of the HOCl with the propylene. Conveniently, the reaction time is less than about 30 minutes, more preferably less than about 15 minutes, to minimize the size of reactor vessel needed to produce a preselected amount of product. Conversion of HOCl in the CSTR is advantageously at least about 90 mole percent, preferably greater than about 98 mole percent, such that the HOCl concentration in the reactor, diluted by water from reacted HOCl solution, does not exceed 0.2 weight percent, preferably less than 0.1 weight percent. Lower conversion levels result in higher yields of chlorinated ketones, such as MCA, from oxidation of the product chlorohydrin, such as PCH. Advantageously, conversion is less than about 99.8 mole percent in the CSTR; higher conversions, though possible, require longer residence times, and thus, larger equipment to produce a preselected amount of product. The residence time required for this conversion is a function of the reaction temperature, desired conversion level, agitation, excess olefin, reactor pressure (when the olefin is a gas), chlorides level in the HOCl feed, and HOCl feed concentration. For propylene (25 mole percent excess) reaction, as example, with 5 weight percent HOCl, containing 200 ppm chlorides, at 60° C. and 4 atmospheres (405.2 kPa) gauge pressure, using a gas-inducing impeller, 15 minutes are required for 99.5 mole percent conversion of the HOCl in the CSTR.

Step 6 is advantageously carried out in a continuous backmix reactor to minimize the further oxidation of the chlorohydrin with HOCl to a chlorinated ketone, for example oxidation of PCH to MCA as shown in Equation 13. Surprisingly, we have discovered that reaction of propylene for example with low chlorides HOCl solutions in a plug flow or batch type reactor results in unacceptably high MCA selectivity of greater than about 1 percent which compares with less than about 0.2 percent selectivity when using a continuous stirred tank reactor according to the practice of the invention. MCA or ketone yields greater than about 0.2 mole percent are undesirable because of their reaction with base to form acetol (1-hydroxypropanone). See Equation 18, Step 7. Increased acetol undesirably increases organic compound level in the effluent brine of Step 7. To control the MCA selectivity for example at 0.2 mole percent or less, the steady-state HOCl concentration in the CSTR is controlled at 0.2 weight percent or less, preferably less than 0.1 weight percent. The steady-state HOCl concentration is controlled by a combination of dilution of the feed HOCl solution with the reactor contents (a function of HOCl feed concentration, feed rate, and reactor volume) and of the reaction kinetics (a function of temperature, pressure, gas-liquid contact (mixing), reactant concentrations, and reaction time).

A backmix reactor is defined as a reactor in which the reaction products are intimately mixed with the feed materials resulting in uniform product and reactant concentrations throughout the reaction vessel. In addition a continuous backmix reactor has product and reactant concentrations in the exit product line equal to the concentrations within the reactor. This concentration is referred to herein as the uniform steady-state concentration. This means that samples taken from any location within the reactor or exit product line analyze to have the same composition. An example of a continuous reactor of this type is commonly referred to as a continuous stirred tank reactor or CSTR.

The HOCl solution from the absorber is preferably fed to a CSTR along with the olefin. A CSTR advantageously includes a vessel having a top head, that is, for example flat, ellipsoidal, or spherical in shape, preferably having at least 6 entry ports (more or fewer entry ports are optionally used) for reactant feeds, an agitator, gas vent, liquid recycle return, and pressure, temperature, and level measurement devices, and a bottom, preferably, ellipsoidal or spherical head advantageously having at least one port for liquid removal from the vessel; between the top and bottom there are advantageously straight walls in a cylindrical shape, optionally having inlets and/or outlets for pressure, temperature, and level measurement devices. Optionally, and preferably, the vessel is jacketed for heat transfer purposes with inlet and outlet ports in the jacket for the circulation of a heat transfer fluid. Inside the vessel, there is a stirring means, advantageously an agitator (used in this discussion as illustrative of the possible stirring means which also include e.g. a venturi mixer). Preferably, the stirring means is smaller than a vertical dimension of the vessel such that when the stirring means is covered with liquid there is a vapor space above the liquid. Optionally, inside the reactor are 2 or more vertical baffles along the straight walls of the vessel. Optionally, outside the reactor there are advantageously a heat exchanger, e.g. for cooling (i.e., removal of part of the heat of reaction), and a recycle pump for recycling product from the bottom of the reactor vessel through the heat exchanger and back to the top of the reactor vessel with discharge either above or below the liquid level in the vessel. The recycle pump advantageously has a suction and at least one discharge line, the former connected to the reactor vessel advantageously in the centerline of the bottom head of the reactor vessel and the latter connected to the heat exchanger and then to the vessel advantageously in the top head. Product is also removed from the reactor via the discharge of the recycle pump at a rate sufficient to maintain a constant level in the reactor. Preferably, when a gas is to be introduced, there is a sparger for the gas, preferably beneath the agitator impeller. In the case of a liquid olefin, such as allyl chloride, the liquid would also be introduced below the agitator impeller. The liquid hypochlorous acid stream advantageously enters the reactor through the top head of the reactor or through a recycle line (for example, the suction of the recycle pump).

Advantageously, the CSTR is designed to achieve efficient gas-liquid contacting. Commercial agitators designed for gas dispersion such that the gas bubbles are kept in continuous contact with the liquid, such as a Chemineer model CD-6 agitator commercially available from Chemineer, Inc. or a Lightnin model A-315 agitator commercially available from Mixing Equipment Company are preferably used. Enhancement of gas/liquid contacting advantageously is achieved by use of gas-inducing contactors, especially impellers as agitators, such as hollow shaft agitators or the Linde Advanced Gas Reactor (AGR) helical screw type agitator commercially available from Praxair Inc. or other helical screw contactor with a draft tube. Agitation is advantageously axial: pulling liquid from the top of the reactor along the axis of the agitator and pushing the flow down to the bottom of the vessel with circulation going up along the walls of the vessel. The downward thrust of the agitator catches the gas (or liquid) from the sparger or gas inlet means located below the agitator, resulting in the desired gas dispersion or liquid mixing. Gas-inducing contactors, especially impellers additionally draw gas from the vapor space of the reactor and discharge it below the bottom agitator blade, thus recycling olefin, which escapes from the reacting solution, back into the solution. This recycle is preferably achieved internal to a reaction vessel containing the solution for efficiency, but is suitably accomplished external to the vessel for instance by an external recirculating blower or compressor. Thus, gas-inducing contactors, particularly impellers, are the preferred technology for the recycle of gaseous olefin because recycle is internal to the vessel. Gas bubbles form in the CSTR but are preferably kept as small as possible because smaller gas bubbles enhance mass transfer and, therefore, reaction rate. Bubbles are kept small by means within the skill in the art such as sparger design, agitation rate, and agitator design mentioned above and by high pressure. Adjusting these parameters to achieve a desirable bubble size is within the skill in the art for instance as discussed by Y. T. Shah in "Design Parameters for Mechanically Agitated Reactors", *Advances in Chemical Engineering*, James Wei, ed., vol. 17, Academic Press, New York (1991) pp. 1–31, 169–206, which reference also is illustrative of gas inducing contactors within the skill in the art.

Conversion of HOCl is optionally completed (to about 100 mole percent) in a secondary plug flow type reactor following the CSTR. This plug flow reactor advantageously is a piece of pipe, or other vessel which gives plug flow characteristics, with a residence time sufficient for HOCl reaction with the olefin. For the CSTR conditions given for propylene, for example, an advantageous plug flow reactor has about 1 minute residence time. There is advantageously about 98 to about 99.8 mole percent conversion in the CSTR and an additional about 0.2 to about 2 mole percent conversion of HOCl in the plug flow reactor when it is used.

Propylene chlorohydrin (PCH) selectivity (based on propylene), for example, after the CSTR and under the preferred CSTR conditions increases to greater than about 6 mole percent, while the propylene dichloride (PDC) selectivity decreases to less than about 2 mole percent as compared to PCH selectivity of less than about 94 mole percent and PDC selectivity of greater than about 4 mole percent for conventional chlorohydrin manufacture (as represented, for instance by the teachings in *Kirk-Othmer Encyclopedia of Science and Technology*, Third Edition, vol. 19, p. 254, (1982)). A low level of conversion in the plug flow reactor results in overall selectivities after the plug flow reactor substantially the same as for the CSTR. Because a low-chloride HOCl solution is used, the selectivity to by-product chlorinated organic compounds, including for example propylene dichloride (PDC) from propylene, is advantageously low, that is PDC is preferably below about 4 mole percent, preferably below about 2 mole percent, more preferably below about 1 mole percent, which concentrations are preferably below those produced when higher concentrations of chloride ion are present such as found in the conventional chlorohydrin manufacture as represented by *Kirk-Othmer Encyclopedia of Science and Technology*, Third Edition, vol. 19, p. 254, (1982). Other by-product selectivities (based on propylene), such as for bis(chloroisopropyl)ether (DCIPE), dichlorohydrin (DCH), and monochloroacetone (MCA), are preferably kept low, e.g. less than about 2.0 mole percent DCIPE, 0.5 mole percent DCH, and 0.2 mole percent MCA. Surprisingly, we discovered that reaction of propylene, for example, with low chlorides HOCl solutions in a plug flow or batch type reactor results in unacceptably high MCA (ketone) selectivity of greater than 1 percent which compares with less than 0.2 percent selectivity when using the CSTR according to the practice of the invention. MCA or ketone yields greater than 0.2 percent are undesirable due to reaction with base (see Equation 18 in Step 7) to form acetol (1-hydroxypropanone). Increased acetol undesirably increases the organic level in the effluent brine of Step 7.

In a most preferred embodiment, discharge (vapor and liquid) from the CSTR reactor or the plug flow reactor, if used, containing for example about 6.5–8.5 weight percent PCH at 60°–80° C., enters a degassing vessel to vent any unreacted propylene or chlorine gas. Chlorine gas is present as a result of the equilibrium of chlorine, chloride, $H^+$, and HOCl in the process liquid. With low chlorides in the HOCl, the chlorine concentration is advantageously below saturation such that little or no chlorine gas is evolved. The flow of discharge enters the top of the degassing vessel, a pressure vessel with 1–5 minutes residence time. The vessel is optionally operated under slight vacuum (about 650 mm Hg absolute pressure (86.7 kPa)) to aid in the degassing of dissolved gases, such as propylene. Recycle or agitation are not required on the vessel, nor is heat exchange (heating or cooling) needed.

The degassing vessel has an overhead vapor vent which is preferably cooled e.g. using a shell and tube heat exchanger cooled by cooling water or another process stream to 40°50° C. to condense and reflux any flashed water and organic compounds back to the degassing vessel. The vent gases (uncondensed gases) then preferably pass through a lime scrubber or other means to remove any chlorine gas. Any scrubbing apparatus or equipment within the skill in the art of gas scrubbing with liquids e.g. using a packed column with either cocurrent or countercurrent gas/liquid contacting is advantageous. Remaining olefin, for example propylene and including inert gases, is advantageously partially recycled to the HOCl/olefin reactor (Step 6) with the remainder going to a burner. The desirable amount of gas going to the burner depends primarily on purity of raw materials. For example, use of polymer grade propylene (less than 0.5 percent by weight propane) instead of chemical grade propylene (about 5 percent by weight propane) results in a significantly lower purge requirement (as measured in volume of recycle gas) to remove the propane gas. The material exiting the bottom of the degassing vessel, is for instance about 6.5–8.5 weight percent propylene chlorohydrin and less than about 0.5 weight percent by-product chlorinated organic compounds and is advantageously conveyed, for instance by pumping, to the epoxidation reaction (Step 7).

7) Optionally contacting the olefin chlorohydrin with a base to produce a corresponding alkylene oxide and a salt solution;

The major desired reaction is that of chlorohydrin with sodium hydroxide or optionally calcium hydroxide to yield the corresponding epoxide. There are, however, a number of side reactions. Epoxides hydrolyze to glycols, for instance propylene oxide (PO) hydrolyzes to propylene glycol (PG). Dichloropropanol (DCH) is converted to epichlorohydrin (Epi) with further hydrolysis to glycidol. MCA is converted to acetol (1-hydroxypropanone). PA (propionaldehyde) often forms during dehydrochlorination of PCH and then undergoes aldol condensation to 2M2P (2-methyl-2-pentenal). Isomerization of the epoxides to aldehydes and ketones and various aldol condensation reaction products also occur. The major reactions are illustrated for the chemicals present during manufacture of propylene oxide:

| | |
|---|---|
| PCH (1)+NaOH (1)→PO (1)+NaCl (1)+H$_2$O (1) | EQUATION 14 |
| PO (1)+H$_2$O (1)→PG (1) | EQUATION 15 |
| DCH+NaOH→Epi+NaCl+H$_2$O | EQUATION 16 |
| Epi+NaOH→H$_2$C(O)—CH—CH$_2$OH+NaCl | EQUATION 17 |
| H$_3$C—C(O)—CH$_2$Cl+NaOH→H$_3$C—C(O)—CH$_2$OH+NaCl | EQUATION 18 |
| PCH+NaOH→PA+H$_2$O+NaCl | EQUATION 19 |
| PA+PA→H$_3$CC(CH$_3$)=CHCH$_2$CH=O | EQUATION 20 |

In Step (7) of contacting the chlorohydrin with an aqueous solution of a base such as sodium hydroxide or an aqueous slurry of calcium hydroxide to produce an epoxide from the chlorohydrin, said epoxide being in an aqueous solution of sodium chloride or calcium chloride, respectively, the amount and concentration of hydroxide are suitably any which result in formation of the corresponding epoxide. For this purpose, the amount of base, preferably hydroxide, is advantageously at least sufficient to epoxidize the chlorohydrin and DCH and carry out the substitution and hydrolysis reactions mentioned above, preferably at least about 1.005 times stoichiometric based on the HOCl fed to the reactor of Step 6, more preferably at least about 1.01 times stoichiometric based on the reactions for example represented by Equations 14, 16, 17, and 18 to ensure that all the PCH reacts to form PO. The excess hydroxide is beneficial to reduce the rate of hydrolysis of PO to PG as compared to the rate under acidic conditions. An alkali metal hydroxide is preferably used to maximize yield of PO from PCH and to eliminate the difficulties associated with suspended solids in for example lime slurries as described by E. Bartholome in U.S. Pat. No. 3,886,187 (May 27, 1975).

The concentration of hydroxide in the feed to the epoxidation reactor is that sufficient to result in epoxide formation, and a solution after stripping of the propylene oxide and other organic compounds having a pH of at least about 11. A concentration of at least about 1 weight percent metal hydroxide is preferred, more preferably at least about 4 weight percent. Use of higher concentrations (up to, for example, 50 weight percent sodium hydroxide) results in advantages of lower volumes of liquid to process.

Conditions of temperature, pressure and reaction times are not critical; any under which the chlorohydrin and hydroxide react to produce an epoxide are suitably used. To keep unreacted PCH in solution long enough to react to PO, the temperature and pressure are preferably controlled to prevent PCH vaporization, that is less than about 95° C. at one atmosphere pressure (101.3 kPa), azeotropic PCH/water boiling conditions. Conveniently, the temperature is at least about 70° C., more preferably at least about 85° C. to maximize the rate of reaction between base and chlorohydrin and to allow vaporization of the product propylene oxide to minimize the hydrolysis reaction of propylene oxide to propylene glycol.

The rate of PCH reaction with caustic is very fast, requiring about 6 seconds to go to 99.5 mole percent completion under conditions of 90° C. and use of calcium hydroxide slurry as the base (solubility of calcium hydroxide in water limits the hydroxide concentration in solution to about 0.021 mole/liter at 90° C.) and less than 1 second under conditions of 90° C. and use of 8 weight percent sodium hydroxide. See Carra, et al., "Synthesis of Propylene Oxide from Propylene Chlorohydrins—I: Kinetic Aspects of the Process", *Chemical Engineering Series*, vol. 34, pp. 1123–1132, 1979, for a discussion of the kinetics of this reaction. Side reactions are typically completed in the same time frame with the exception of PO hydrolysis to PG which is a function of the PO concentration in solution. PO is preferably vaporized as soon as it is formed to minimize the amount of glycol formed.

8) Optionally separating the alkylene oxide from the salt solution;

Step (8) of separating the epoxide from the aqueous solution of sodium chloride and sodium hydroxide or alternatively the aqueous solution of calcium chloride and calcium hydroxide is achieved by any process which results in separation of the epoxide, which processes are within the skill in the art, such as distillation or steam stripping. Bartholome et al. describe such a process in U.S. Pat. No. 3,886,187 (May 27, 1975) where the reaction product of the chlorohydrin and base (either sodium hydroxide or calcium hydroxide) is fed to the top of a stripping column. An initial separation of the vapor containing propylene oxide, water vapor and some by-product organic compounds and the liquid brine occurs in the head space of the column. The liquid brine then flows downward through either a tray or packed section where steam (about 1–2 kg steam per kg of propylene oxide formed from the saponification of a 5 weight percent propylene chlorohydrin solution) flowing upward contacts the liquid to strip the remaining dissolved propylene oxide from solution. The conditions of this separation are described as preferably 90°–120° C. and 0.6 (60.8 kPa) to 2.0 atmospheres (202.6 kPa) absolute pressure. Vapor containing propylene oxide, water vapor (steam), and by-product organic compounds is taken overhead, where a partial condensation is optionally carried out to reflux part of the water to the stripping column, but little or no propylene oxide is refluxed to minimize propylene glycol formation. The remainder of the vapor is then condensed before final purification of the propylene oxide.

Any glycol and acetol, for example, remain in the resulting sodium chloride brine which preferably exits the bottom of the column (bottoms). The other organic compound by-products are less than 10 ppm by weight each in the bottoms.

9) Optionally removing chlorates from the chloride brine from at least one of Steps 3 or 4 by contacting the chlorates with acid to convert the chlorates to chlorine; and Chlorates in the chloride brine from the HOCl stripper (Steps 3 and 4) are optionally reduced by a variety of processes within the skill in the art.

Preferably, however, chlorates are advantageously removed by reaction with HCl or other acids to yield HOCl (Equation 21) with further reaction to chlorine (Equation 22) which is optionally stripped from the brine (Equation 24). The reactions are illustrated by:

| | |
|---|---|
| HClO$_3$ (1)+2HCl (1)→3HOCl (1) | EQUATION 21 |
| HOCl (1)+HCl (1)→Cl$_2$ (1)+H$_2$O (1) | EQUATION 22 |

The overall reaction is then:

| | |
|---|---|
| HClO$_3$ (1)+5HCl (1)→3Cl$_2$ (1)+3H$_2$O (1) | EQUATION 23 |
| Cl$_2$ (1)→C$_2$ (g) | EQUATION 24 |

R. Dotson reports in "Kinetics and Mechanism for the Thermal Decomposition of Chlorate Ions in Brine Acidified with Hydrochloric Acid", *Journal of Applied Chemical Biotechnology*, vol. 25, 1975, pp. 461–464, that Equation 21 is the rate limiting step and that the kinetics are represented by the following expression with units of moles/liter (mole/L), °K., and minutes:

$$-d[ClO_3^-]/dt = 1.83 \times 10^{18} [ClO_3^-][H^+]^2 e^{(-35056/RT)} e^{[Cl^-]}$$

EQUATION 25

The above expression is advantageously used to design an advantageous reactor for reduction of chlorates. For example, for 99 mole percent reduction in chlorates, 140° C., pH=1, [Cl$^-$]=4 mole/liter, the required residence time is 16.5 minutes. The reaction conditions are advantageously adjusted to meet the residence time requirements of the process. For example, higher temperature and lower pH lowers the residence time while lower temperature and higher pH lengthens the time required for reduction of the chlorates.

Alternatively, chlorate reacts with sulfurous acid:

$$HClO_3 + 3H_2SO_3 \rightarrow 3H_2SO_4 + HCl$$

EQUATION 26

This reaction is discussed by E. H. Gleason et al. in "Kinetics of the Chlorate-Sulfite Reaction", *Journal of Physical Chemistry*, vol. 61, April 1957, pp. 447–450. The reaction rate is described as follows with units of liters, moles, °K., and seconds:

$$-d[ClO_3^-]/dt = 3.3 \times 10^7 [ClO_3^-][H_2SO_3] e^{-11000/RT}$$ EQUATION 27

Advantageous exemplary reaction conditions for the reaction using sulfurous acid include a pH of about 2, a temperature of about 60° C., and 4.5 minutes reaction time for 99 mole percent reduction in chlorate. Gleason reports the reaction is carried out preferably with an excess of acid above stoichiometry to minimize the time required for reaction completion. A range of conditions advantageous for 99 mole percent reduction in chlorate content includes a pH of about 1–3, a temperature of about 40°–100° C., and reaction times of about 5 seconds at the lower pH and higher temperatures to about 130 minutes at higher pH and lower temperatures. These processes illustrate advantageous processes within the skill in the art for use in the present invention.

The use of hydrochloric acid to reduce chlorates to chlorine has the advantage of allowing recycle of the chlorine produced, e.g. to Step 1 or to Step 4, of the process of the invention, thus increasing the overall yield from chlorine. In addition, hydrochloric acid is a more readily available raw material than sulfurous acid. The use of sulfurous acid has the advantage of milder operating conditions and reaction times, resulting in smaller equipment and lower energy requirements. After the reaction is complete, the product acidic calcium chloride brine is advantageously neutralized, preferably with either calcium hydroxide slurry to a pH of about 5–6.5 or sodium hydroxide to a pH of about 5–8 before discharge. The resulting brine is optionally cooled for energy recovery prior to discharge.

10) Optionally recycling the chlorine to at least one of Steps 1 or 4.

An advantage of reducing the chlorates to chlorine using HCl is that the chlorine is optionally degassed from the solution and recovered for use, for example, in producing the hypochlorite in Step 1 or in the stripping column of Step 4.

In addition to the process Steps 1–10, product epoxide and solutions resulting from the various reactions are optionally and advantageously further purified by means within the skill in the art. For instance, the epoxide is advantageously separated from by-product halogenated organic compounds by processes such as that disclosed by Naugle (U.S. Pat. No. 3,282,966) which describes one advantageous process using distillation equipment within the skill in the art for purifying propylene oxide produced from a chlorohydrin process. An unpurified stream, composed of 40 percent to 90 percent by weight propylene oxide and a balance of water, propylene dichloride and other organic impurities, is purified to provide a greater than 99 weight percent pure propylene oxide product stream. An overview of this process begins with feeding the unpurified propylene oxide stream to a distillation column which fractionates said stream into a bottoms fraction consisting of the bulk of the water, propylene dichloride and other organic impurities and into an overheads fraction consisting of 95 weight percent to 99.9 weight percent propylene oxide, 0.1 weight percent to 5 weight percent water and 0.1 weight percent to 2 weight percent other organic impurities. The overheads fraction is then fed to a second distillation column which fractionates said stream into a bottoms fraction consisting of 10 weight percent to 90 weight percent propylene oxide and a balance of water and propionaldehyde. The overheads fraction from this second distillation column consists of more than 99 weight percent propylene oxide, only trace quantities of water and less than 50 ppm by weight of other impurities. Recycle and further processing of the bottoms fraction from this second distillation column is performed to recover the propylene oxide contained therein.

Also advantageously by-product halogenated organic compounds are separated from each other and from water such as separation and purification of propylene dichloride (PDC), epichlorohydrin (Epi), or dichloroisopropyl ether (DCIPE), by distillation or separation techniques within the skill in the art.

Additionally, by-product organic compounds such as propylene glycol present in the brine of Step 8 are advantageously removed through any oxidation, extraction or absorption process within the skill in the art. At the low organic species concentrations present in this material stream, biological oxidation is a preferred technique. In the application of biological oxidation to removal of the organic by-products in the NaCl brine (or optionally CaCl$_2$ brine), selected microorganisms, for which the organic contaminants are not toxic, are able to metabolically degrade the organic compounds present therein in a controlled environment by means within the skill in the art. Desired final products from the decomposition of the organic by-products contained in the brine are carbon dioxide and water.

Those skilled in the art will recognize that in each step of the process of the invention there are chemicals which are often corrosive to steel and the like; therefore, apparatus in contact with such chemicals is advantageously made of or lined with materials resistant to the chemicals such as polytetrafluoroethylene, polyvinylidene fluoride, titanium, or other resistant material.

Practice of the process of the invention advantageously results in improved yields, for example, to PCH and lower yields of PDC, while maintaining or reducing the yields to the other chlorinated organic compounds as compared to the art described in *Kirk-Othmer Encyclopedia of Chemical Technology*, Third Edition, vol. 19 (1982), pp. 246–274. This is accomplished while operating at high (at least about 6.5 weight percent) PCH product concentrations and at temperatures at least about 60° C. in Step 6. Shen et al. (U.S. Pat. No. 5,146,011) disclose the use of low chlorides aqueous hypochlorous acid solutions in reaction with propylene to produce PCH at temperatures up to 55° C. Practice of the process of the present invention advantageously results in less than about 2 mole percent of the propylene being converted to PDC, preferably less than about 1 mole percent yield to PDC and less than about 0.2 mole percent to MCA, while employing reaction temperatures of about 60° C., preferably about 70° C. with final PCH product concentrations of about 6.5–8.5 weight percent.

Practice of the invention advantageously maintains oxidation of the product chlorohydrin such as propylene chlorohydrin (PCH) with HOCl to a chlorinated ketone such as monochloroacetone (MCA) to preferably less than about 0.2 mole percent yield based on propylene reacted. This is accomplished by maintaining the uniform steady-state HOCl concentration in the reactor of Step 6 at less than 0.2 weight percent, preferably less than 0.1 weight percent and a reactor temperature less than about 100° C., preferably less than about 90° C. In the practice of the invention, the low HOCl concentration in the reactor is preferably achieved in a continuous stirred tank reactor (CSTR) as disclosed herein such that the steady-state HOCl concentration in the reactor is maintained at the desired levels by optimally controlling feed rates, temperature, pressure, and agitation rates.

The quantity of waste water to be treated for organic compounds removal is advantageously reduced in the practice of the invention. Aqueous salt solutions from the first four steps do not contact organic compounds; therefore, removal of organic compounds prior to discharge is not required. Also, less water (50–65 weight percent as much) is used in the reaction of aqueous HOCl with olefin according to the practice of the invention than is disclosed by Kirk et al. in "Propylene Oxide", *Kirk-Othmer Encyclopedia of Chemical Technology*, third edition, vol. 19 (1982), pp. 246–274. The main reason for reduced volume is the reduced water used in the hypochlorination step (Step 6) as illustrated by the higher product PCH concentrations of 6.5–8.5 weight percent in the CSTR compared to 4–5.5 weight percent in the reactors described by Kirk et al.

The following examples are included to illustrate but not limit the invention. Examples of the invention (Ex.) are designated numerically while comparative samples (C.S.) are designated alphabetically and are not examples of the invention. In these examples, all ratios, parts, and percentages are by weight unless otherwise designated.

EXAMPLE 1: EFFECT OF pH ON THE REACTION OF CALCIUM HYDROXIDE SLURRY WITH CHLORINE TO FORM $Ca(OCl)_2$

A 6.64 weight percent calcium hydroxide-in-water slurry (hereinafter feed) at 19.0 L/hr is reacted with varying amounts of gaseous chlorine (as indicated in Table 1) in a pump reactor consisting of a centrifugal pump equipped with a recycle loop and an in-line static mixer placed on a product discharge line coming of off the recycle loop. Downstream of the static mixer, the reactor product is cooled in a titanium heat exchanger, and then filtered to remove solids before being stored for later use.

Specifically, the reactor combines a magnetically driven centrifugal pump (commercially available from March Manufacturing Inc. under the trade designation March model, MDX-MT3 rated at 28.13 liters/minute at zero head and 3500 rpm) with a ⅜ inch (9.525 mm) diameter piece of tubing made from fluorocarbon polymer (commercially available from E. I. du Pont de Nemours & Co. under the trade designation Teflon™ PFA) through which the reactor contents (predominantly aqueous calcium hypochlorite product with small amounts of unreacted calcium hydroxide, chlorine and insoluble solids such as calcium carbonate, and silicates) are recycled back to the pump inlet (at approximately a 40:1 to 50:1 ratio of product to feed). A ½ inch (12.7 mm) polyvinyl chloride (P.V.C.) pipe static mixer (commercially available from Koflo Corporation under the trade designation Koflo model 1/2-80-4-12-2) is installed on a ⅜ inch (9.525 mm) Teflon™ PFA fluoropolymer discharge line connected to the pump recycle loop to help ensure completion of the reaction.

The pH of the reactor contents is measured on both the recycle loop and on the discharge line of the reactor (downstream of the static mixer) by a pH controller commercially available from Cole-Parmer Instrument Company under the trade designation Cole-Parmer model 5656-00 LED pH controller. A thermocouple is placed on the recycle loop to measure the temperature of the reactor contents, while a second thermocouple is installed downstream of the heat exchanger to measure the temperature of the cooled, unfiltered product.

The cooled reactor product (about 20° C.) is filtered to remove solids (mainly calcium carbonate, silicates and unreacted calcium hydroxide) by two filters in series before being stored. The first (primary) filter is a 1 micron (1 micrometer) polypropylene liquid filter bag commercially available from Minnesota Mining and Minerals Corp. under the trade designation p/n 2P01PPRWH and the next (secondary) filter is a 10 in (254 mm), single open-ended filter cartridge using 1.2 micron (1.2 micrometer) polypropylene filter media. Following filtration, the clarified product is placed in a nitrogen padded polyethylene storage drum which is painted to provide opacity.

Once the reactor pH, as measured on the discharge line, has reached the level shown in Table 1, product samples (each weighing about 100 gm) are collected by opening a sample valve located downstream of the secondary filter mentioned above. The samples are analyzed for calcium hypochlorite $(Ca(OCl)_2)$ content by iodometric titration, and for chlorate ion $(ClO_3^-)$ concentration by ion chromatography. Trace amounts of calcium hydroxide are detected by titration with 0.1N HCl until a recurring flash of color provided by phenolphthalein indicator is absent. The results are summarized in Table 1.

TABLE 1

EFFECT OF pH IN CHLORINE/LIME REACTION

| Chlorine (kg/hr) | pH | $Ca(OCl)_2$ (weight percent) | $Ca(OH)_2$ (weight percent) | $ClO_3^-$ (ppm) |
|---|---|---|---|---|
| 1.012 | 11.0 | 5.20 | 0.21 | <10 |
| 1.180 | 10.8 | 5.81 | 0.11 | <10 |
| 1.185 | 10.5 | 5.89 | nd | <10 |
| 1.194 | 10.0 | 5.99 | nd | <10 |
| 1.207 | 9.0 | 5.94 | nd | 30 |
| 1.253 | 8.0 | 5.77 | nd | 1495 |
| 1.321 | 7.0 | 3.99 | nd | 10895 |

Note:
Reactor temperature = 43.9° C. and chilled product temperature = 19.7° C. for all runs.
nd = none detected.

These data show chlorates increasing and calcium hydroxide conversion to hypochlorite increasing as pH is reduced. Advantageously, the conversion of lime to hypochlorite is maximized while minimizing formation of chlorates. According to these data, a preferable pH for reactor operation is 9–11 with a more preferred pH range of 10–11. The pH of the calcium hydroxide slurry prior to chlorination is about 12.

EXAMPLE 2: PRODUCTION OF LOW CHLORATE CALCIUM HYPOCHLORITE FROM THE REACTION OF CALCIUM HYDROXIDE SLURRY WITH CHLORINE

The procedure of Example 1 is repeated using 9.08 kg/hr of a 4.58 weight percent calcium hydroxide slurry reacted with 0.908 kg/hr chlorine at a pH of 10.35 and ambient temperature (about 30° C.)and pressure. After filtration of the reactor product (using the same filtration process described in Example 1), analysis of the product shows 3.93 weight percent calcium hypochlorite, 0.18 weight percent calcium hydroxide, and 62 ppm chlorate (less than 1 percent yield loss) with the balance being water and trace amounts of silicates and carbonates.

EXAMPLE 3: REACTION OF LIQUID CHLORINE WITH LOW CONCENTRATION CALCIUM HYPOCHLORITE SOLUTIONS TO FORM HOCl USING A CENTRIFUGAL PUMP AS A BACKMIX REACTOR

The reactor used in this Example is a magnetically driven centrifugal pump commercially available from March Manufacturing Inc. under the trade designation March model MDX-MT3 having inlet and exit ports, a cavity, and, in the cavity, an impeller on a pump shaft, said pump rated at 28.13 liters/minute at zero head and 3500 rpm. The pump inlet is connected to one run port of a 0.84-inch (21.3 mm) outside diameter (0.5 inch nominal pipe size) polyvinylidene fluoride (P.V.D.F.) tee having two run ports, that is, openings on a pipe fitting connected to another, similar opening on the same fitting by a straight line, and one branch port, that is an opening oriented 90 degrees relative to the run ports. A ⅛ inch (3.175 mm) outside diameter piece of tubing made from fluorocarbon polymer, commercially available from E. I. du Pont de Nemours & Co. under the trade designation Teflon™ PFA fluoropolymer, is connected to the second run port of the aforementioned tee and passes completely through the tee and pump inlet port to a termination point inside the pump cavity and resting on an imaginary axial line defined by the pump shaft. This tubing is used to feed fresh liquid chlorine into the reactor. The remaining branch port of the first tee is close coupled to the run port of a second 12.7 mm P.V.D.F. tee. A ¼ inch (6.350 mm) diameter piece of tubing also made from Teflon™ PFA fluoropolymer is connected to the other run port of the second tee. This tubing is used to feed fresh calcium hypochlorite solution to the reactor. Another 6.350 mm diameter piece of Teflon™ PFA fluoropolymer tubing is connected to the remaining branch port of the second tee. This tubing is used to recycle the reactor contents back to the feed inlet where it is mixed with the incoming fresh calcium hypochlorite.

The exit port of the reactor is connected to another P.V.D.F. tee like the inlet port. Most of the reactor contents are recycled back to the inlet through the run of this tee (at approximately a 30:1 to 40:1 recycle-to-feed hypochlorite solution ratio) while the balance is sent through the branch port of the initial exit tee and into the branch port of a second, close coupled P.V.D.F. tee. The first run port of this second exit line tee is connected to a 3.175 mm Teflon™ PFA fluoropolymer tube for sampling the reactor contents, while a Teflon™ fluoropolymer back pressure regulator commercially available from MACE Products under the trade designation MACE model 975 Teflon™ Backpressure Regulator is connected to the remaining run port and is used to control reactor pressure by regulating the amount of reactor product sent forward into the HOCl distillation unit. A pressure gauge is mounted on the regulator for measurement of the reactor pressure, and a thermocouple is mounted downstream of the regulator for the temperature measurement of the reactor contents. The entire assembly is traced (in a spiral fashion) with copper tubing carrying a cold brine refrigerant at 0°–10° C. and insulated. This design allows for minimizing the residence time of the reactor contents (less than 40 sec) and avoids localized zones of high HOCl/ $Ca(OCl)_2$ concentration which would unfavorably enhance the decomposition rate of HOCl to chlorates. The centrifugal pump operated in this configuration is considered a backmix reactor.

Chilled calcium hypochlorite solution (4.15 weight percent, 85 ppm chlorates), prepared by the procedure of Example 2, is fed at a rate of 11.4 kg/hr and 1.5° C. to the reactor along with 0.607 kg/hr liquid chlorine (30 mole percent excess chlorine) at 4.2° C. Reactor pressure is 55 psig (379 kPa gauge) with a temperature of 10.4° C. The pH of the reaction mixture is 3.65, with an ORP (Oxidation-Reduction Potential) of 1196 mV as measured by a combination pH/ORP probe mounted on the reactor recycle line. Reactor product samples weighing approximately 2 g each are taken from the tube for sampling reactor contents and instantaneously quenched in tared bottles containing a known amount (between 15 g and 25 g) of 0.1N caustic. Iodometric titration of the quenched product provides a composition analysis of 6.538 weight percent HOCl (HOCl plus unreacted chlorine). Ion chromatography analysis shows 370 ppm chlorates which represent a yield loss of 1.9 mole percent and thus an HOCl yield of 98.1 mole percent.

This example shows high HOCl reactor yields are possible using a centrifugal pump as a backmix reactor operating under conditions of low temperature (10° C.), pressure above the vapor pressure of chlorine (379 kPa gauge), low pH (3.65), and a hypochlorite feed concentration of 4.15 weight percent. Under these conditions, the centrifugal pump provides sufficient micromixing to achieve a desired yield of at least about 80 mole percent.

EXAMPLES 4-1 THROUGH 4-8 AND COMPARATIVE SAMPLE A: REACTION OF LIQUID CHLORINE WITH HIGH CONCENTRATION CALCIUM HYPOCHLORITE SOLUTIONS TO FORM HYPOCHLOROUS ACID IN MODIFIED CENTRIFUGAL PUMP ACTING AS A BACKMIX REACTOR.

For this example, a modified magnetically driven centrifugal pump is constructed from titanium and used as a backmix reactor. A motor and impeller commercially available from the Mar. Manufacturing Inc. under the trade designation Mar. model, MDX-MT3 pump is used with a custom reactor chamber (illustrated by FIGS. 6 and 7). The reaction chamber is a hollow cylinder of 60 mm diameter and 15 mm height housing the 6 blade radial paddle type impeller from the Mar. pump. A recycle channel, measuring 17 mm in diameter by 20 mm long, is included from the perimeter of the pump to the axis area of the impeller to provide back mixing required of a backmix reactor. In addition 11 baffles, 2 mm titanium rods, are located at equal distances around the perimeter of the impeller to increase the shear forces on the bulk liquid to maintain low pH throughout the solution. These baffles are placed 1 mm from the reactor cavity wall. Performance comparisons without baffles verify yield losses associated with localized high pH regions and show the importance of micromixing as is shown by Comparative Sample A in Table 2.

Liquid chlorine (0.76–3.27 kg/hr) and aqueous calcium hypochlorite (4.36–20.43 kg/hr)at concentrations (10.2–12.5 weight percent) listed in Table 2 are co-introduced to the axial area of the impeller. Temperature readings (10°–45° C.) are taken directly from the reactor mixing chamber through a tantalum thermal well, while pH (less than 4.5) is measured on the recycle loop. Finally reactor pressure (655–965 kPa) is determined with a pressure transmitter on the product line and is sufficient to keep chlorine in liquid phase. Reactor temperature is increased or decreased using glycol flowing through four round channels bored in the reactor body.

Direct measurement of HOCl concentration by iodometric titration and chlorate yield losses by ion chromatography are made for operation of the backmix reactor at high concentration calcium hypochlorite (up to 12.5 weight 5 percent). Yield in excess of 94 percent is demonstrated for reaction temperatures up to 44° C. and mean solution retention time in the reactor up to 34 seconds and ORP are measured as in Example 3 to be 5.88 and 1055, respectively. The reactor product is sampled and analyzed also as in Example 3. HOCl plus unreacted chlorine are 6.86 weight percent. Chlorates are 4250 ppm, and representing a 24.1 percent yield loss.

Even though the reactor temperature is low and chlorine is in excess, the use of gaseous chlorine in this reactor fails to lower the pH sufficiently to minimize HOCl losses to chlorates.

EXAMPLE 5: HIGH YIELD RECOVERY OF HYPOCHLOROUS ACID

Figure 4:
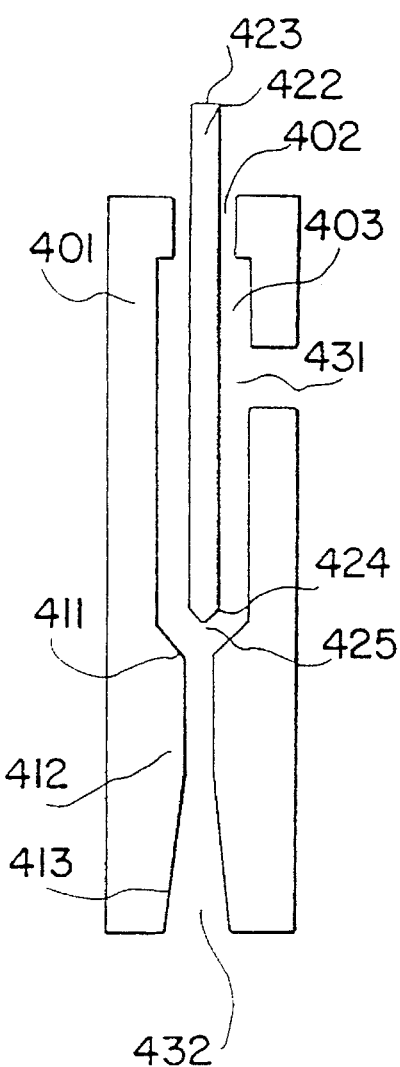
FIG. 4 represents a sectional view of another embodiment of a nozzle for spraying a solution of hypochlorous acid droplets.

Product from the reactor and procedures of Example 3 is fed at 11.9 kg/hr (4.00 weight percent HOCl) to a steam driven atomization nozzle (as illustrated in FIG. 4 and made of glass filled Teflon™ fluoropolymer) mounted vertically

TABLE 2

Titanium Reactor Studies with Baffles

| Ex. or C.S. | Reactor Temp. (C.) | Reactor Pressure (kPa) gauge | Ca(OCl)$_2$ Flow (kg/hr) | Ca(OCl)$_2$ Conc. (weight percent) | Cl$_2$ Flow (kg/hr) | Mole Percent Excess Cl$_2$ | Reaction Time (Sec.) | HOCl Yield (%) |
|---|---|---|---|---|---|---|---|---|
| Ex. 4-1 | 11 | 655 | 9.07 | 12.0 | 1.31 | 19 | 17 | 99.8 |
| Ex. 4-3 | 12 | 689 | 20.43 | 12.5 | 3.27 | 27 | 8 | 99.8 |
| Ex. 4-2 | 12 | 724 | 11.34 | 12.5 | 1.68 | 17 | 14 | 99.5 |
| Ex. 4-4 | 31 | 827 | 9.07 | 10.8 | 1.30 | 30 | 17 | 98.3 |
| Ex. 4-5 | 29 | 965 | 4.36 | 11.8 | 0.76 | 47 | 34 | 96.5 |
| Ex. 4-6 | 40 | 965 | 9.25 | 12.0 | 1.31 | 17 | 17 | 97.5 |
| Ex. 4-7 | 44 | 965 | 5.40 | 11.4 | 0.82 | 33 | 28 | 94.2 |
| Ex. 4-8 | 14 | 714 | 9.07 | 10.8 | 1.56 | 56 | 16 | 100.0 |
| C.S. A | 24 | 724 | 12.26 | 10.2 | 1.73 | 36 | 13 | 66.5 |

Comparative Sample A is not an example of the invention and is run with the same reactor of Examples 4–1 through 4–8 except without baffles in the reactor chamber, hence without sufficient micromixing to achieve a product hypochlorous acid in a yield of at least about 80 percent based on hypochlorite with less than about a 20 percent yield of chlorate. The conditions and results are given in Table 2 and indicate a low recovered yield of 66.5 percent in spite of operation at the favorable reaction temperature of 24° C., pressure of 724 kPa, low residence time of 13 seconds, and 36 mole percent excess chlorine over stoichiometry.

COMPARATIVE SAMPLE B: REACTION OF GASEOUS CHLORINE WITH LOW CONCENTRATION CALCIUM HYPOCHLORITE SOLUTIONS TO FORM HOCl USING A CENTRIFUGAL PUMP AS A BACKMIX REACTOR

The procedure of Example 3 is repeated with 0.608 kg/hr gaseous chlorine (9 mole percent excess chlorine) at 8.5° C. fed to the reactor along with 11.4 kg/hr of 4.78 weight percent calcium hypochlorite solution (containing 185 ppm chlorate ions by weight) at 7.4° C. The reactor pressure is 40 psig (276 kPa gauge) with a temperature of 16.2° C. The pH and pointing downward along the axial center and approximately 762 mm from the top of a glass stripper column (150 mm inside diameter for its length of 3.05 m). In the nozzle, the HOCl is mixed with 6.7 kg/hr of 15 psig (103 kPa gauge) steam. The steam heats the HOCl stream to a temperature of 60° C., and provides the kinetic energy to break up the liquid into fine droplets with a volume median diameter of about 60 micrometers. The resulting spray enters the column operating at 155 mm Hg (20.7 kPa) pressure absolute where HOCl (primarily as Cl$_2$O vapor) is desorbed from the liquid into the vapor, and the vapor is removed overhead and out of the stripper.

The spray nozzle discharge is located 450 mm above a 1.38 m bed of ¼ inch (6.35 mm) ceramic saddle-shaped packing commercially available from Norton Company under the trade designation Intalox™ saddles. Liquid from the spray nozzle (containing water, HOCl, and CaCl$_2$, along with trace amounts of chlorine and calcium chlorate) falls down onto the saddle packing where it is further stripped of HOCl by countercurrent contact with a rising stream containing steam and chlorine vapor. All of the stripped and desorbed HOCl, uncondensed water vapor and unreacted chlorine from both the spray zone and the packed distillation/stripping zone exit the top of the stripper and flow to the bottom of an HOCl absorber column (described hereafter).

Steam (5.7 kg/hr at 205 kPa) is introduced at the bottom of the stripper column as a stripping agent via a glass-filled Teflon™ fluoropolymer steam-jet ejector. The discharge end of the ejector is connected directly to a bottom vapor space of the stripper, about 10 inches (254 mm) below the bed of stripper packing. The chlorine/water vapor inlet of the steam-jet ejector is piped to the top of an absorber (described hereafter). Use of the ejector allows the steam to pull chlorine around in a recycle loop from the HOCl absorber back to the stripper. The resultant stripping vapor stream contains about 10 mole percent chlorine gas which is beneficial for suppressing the rate of chlorate formation in the stripper.

A brine stream, stripped of HOCl, exits the bottom of the stripper column at a rate of 17.2 kg/hr. Analysis of this brine indicates 0.087 weight percent chlorates ($ClO_3-$) and 0.029 weight percent HOCl. The brine stream is analyzed for chlorates and HOCl by the procedures of Example 3. The chlorates and HOCl in the bottom of the stripper represent a combined 9 percent yield loss based on the HOCl in the feed to the stripper.

As mentioned earlier in this example, the overhead vapor from the stripper goes to the bottom of a vertical glass absorber column (150 mm inside diameter, 3.05 m overall length) operating at 150 mm Hg (20 kPa) pressure absolute, and containing two packed sections each filled with ceramic saddle-shaped packing (commercially available from Norton Company under the trade designation Intalox™ saddles). The lower packed section includes a 0.38 m bed of ½ inch (12.7 mm) Intalox™ saddles resting on a packing support approximately 6 inches (254 mm) above the vapor entrance to the absorber. Liquid from the bottom of the absorber is pumped through a shell and tube heat exchanger at 5–10 liters/min using a centrifugal pump. The absorber bottoms are chilled in the exchanger to approximately 5°–10° C. (using ethylene glycol at 0°–3° C. as a refrigerant) and then fed onto the top of the lower packed section where it combines with liquid from the upper packed section. Fresh condensate water at 5° –10° C. is fed at a 11.4 kg/hr rate to the top of the absorber column where it is then distributed across the top of the upper packed section consisting of a 1.3 m (height) bed of ¼ inch (6.35 mm) saddles resting on a perforated packing support approximately 18 inches (46 mm) above the lower section of packing.

Essentially all of the water vapor and the HOCl are condensed in the lower packed section of the absorber. Any remaining amounts of HOCl and/or $Cl_2O$ vapor are recovered in the upper section of packing by countercurrent contact with the chilled condensate. The absorber bottoms liquid (24.01 kg/hr) is analyzed by iodometric titration as 2.49 weight percent HOCl. Excess, unreacted chlorine is vented through the top of the absorber column and to a vacuum source provided by a water eductor. Most of the chlorine vapor exiting the top of the absorber is conveniently recycled back to the bottom of the stripper via the steam-jet ejector previously mentioned. The recovered HOCl yield in the absorber (based on $Ca(OCl)_2$ fed to the reactor as in Example 3) is 91 percent.

This Example shows that hypochlorous acid can be recovered in high yields when quickly separated from the high brine content product exiting from the HOCl reactor by using a stripper/absorber process in which chlorine vapor is recycled between the two columns.

EXAMPLE 6: HIGH YIELD RECOVERY OF HYPOCHLOROUS ACID

The procedure of Example 5 is repeated using 12.0 kg/hr of 5.8 weight percent HOCl fed with 4.1 kg/hr steam to the spray nozzle. The volume median diameter of the liquid droplets is about 80 micrometers. Steam is also fed into the bottom of the stripper at 3.6 kg/hr, and 11.4 kg/hr fresh water is fed into the top of the absorber. The bottoms of the stripper measures 12.36 kg/hr brine with 0.191 weight percent chlorate ions and 0.028 weight percent HOCl. The absorber bottoms measure 20.31 kg/hr of 2.887 weight percent HOCl. The recovered HOCl yield is 87 percent.

This Example also shows that hypochlorous acid can be recovered in high yields when quickly separated from the high brine content product exiting from the HOCl reactor by using a stripper/absorber process in which chlorine vapor is recycled between the two columns.

EXAMPLE 7: HYPOCHLORINATION WITH HOCl IN A CONTINUOUS STIRRED TANK REACTOR (CSTR).

A continuous stirred tank reactor (CSTR), which is a cylindrical 2-liter glass reactor with a hemi-spherical shaped top head and bottom and a diameter to height ratio of 0.4 is used to react propylene gas with low-chlorides HOCl solutions to produce propylene chlorohydrin. An agitation rate of 700 RPM is supplied by two 6-bladed turbine impellers having a diameter of 4 cm and placed 3 cm apart and with the lower impeller 5 cm from the reactor bottom. The reactor is initially charged with 1 liter of low-chlorides water having less than 50 ppm chloride. The reactor is maintained at atmospheric pressure (101.3 kPa absolute) and 25° C.

Low-chlorides HOCl solution, prepared by the process of Example 5 having less than 200 ppm chloride and a concentration of HOCl indicated in Table 3, is continuously fed to the top of the reactor at a rate to give the indicated residence times in Table 3 when the reactor volume is maintained at 1 liter. Propylene gas enters the reactor below the bottom agitator impeller at a rate of 25 mole percent excess over that stoichiometric with the HOCl. The excess propylene vapor exits the top of the reactor through a condenser that refluxes any condensate back to the reactor with uncondensed vapor passing through a cold trap and sodium hydroxide scrubber. The clear aqueous product solution, containing the propylene chlorohydrin and other organic compounds, is continuously removed from the reactor and collected in a tank. After 5 residence times (for example 75 minutes for a 15 minute residence time run), the product flow is diverted to a sample bottle for analysis by gas chromatography using a flame ionization detector. The average molar selectivity data are obtained based on propylene and are listed in Table 3:

TABLE 3

MOLE PERCENT SELECTIVITIES RESULTING FROM HYPO-
CHLORINATION OF PROPYLENE WITH LOW-CHLORIDES HOCl
IN A CSTR REACTOR AT 25° C. AND ATMOSPHERIC PRESSURE

| Residence Time, min. | weight percent HOCl in Feed | Chlorides in feed, ppm | weight percent HOCl in Exit | PCH | PDC | DCH | DCIPE | MCA |
|---|---|---|---|---|---|---|---|---|
| 15 | 1.0 | 100 | 0.06 | 98.4 | 0.90 | 0.46 | 0.15 | 0.09 |
| 15 | 2.0 | 100 | 0.19 | 98.1 | 0.77 | 0.74 | 0.30 | 0.12 |
| 30 | 3.0 | 500 | 0.00 | 97.2 | 1.82 | 0.40 | 0.50 | 0.13 |
| 30 | 3.9 | 500 | 0.00 | 97.4 | 1.41 | 0.45 | 0.67 | 0.06 |

PCH is propylene chlorohydrin, the desired product.
PDC is propylene chloride.
DCH is dichloropropanol.
DCIPE is dichloroisopropyl ether.
MCA is monochloroacetone These data show that a CSTR is an effective reactor for reacting HOCl and an olefin like propylene. The DCIPE is a function of the feed HOCl concentration.

EXAMPLE 8: HYPOCHLORINATION WITH HOCl IN A CONTINUOUS STIRRED TANK REACTOR (CSTR) AT ELEVATED TEMPERATURES AND PRESSURE.

The procedure of Example 7 is repeated except that a CSTR which is a vertically mounted cylindrical 2-liter titanium reactor with a flat stainless steel head plate and a diameter to height ratio of 0.4 is used. An agitation rate of 1000 RPM is supplied by two types of impellers (1) a gas inducing impeller and (2) a non-gas inducing impeller. The gas inducing impeller consists of a ⅜-inch (9.5 mm) diameter hollow shaft glass tube with four ¼-inch (6.35 mm) diameter hollow glass tubes attached perpendicular to the bottom of the shaft and a 4-bladed pitched blade turbine impeller placed 1 cm above the hollow tubes. The diameter of both impellers is 4 cm. Four holes are drilled perpendicular to the shaft 19 cm from the bottom of the gas inducing impeller. These four holes allow vapor from the headspace of the reactor to flow down the hollow shaft for discharge through the hollow gas-inducing impeller into the liquid. Reactant feeds and product takeoff are the same as in Example 7 with 2 weight percent HOCl feed concentration having less than 200 ppm chloride. Overhead vapors pass through a reflux condenser and cold trap to collect any vaporized water and organic compounds. For the non-gas inducing impeller, the four holes on the shaft are covered with heat-shrink Teflon™ fluoropolymer tape. The average molar selectivity (based on propylene) data obtained in the CSTR at a 15 minute residence time, 40 psig (275.6 kPa gauge) are listed in Table 4.

TABLE 4

MOLE PERCENT SELECTIVITIES BASED ON PROPYLENE RESULTING
FROM HYPOCHLORINATION OF PROPYLENE WITH LOW-CHLORIDES
HOCl IN A CSTR REACTOR AT 40 PSIG (275.6 kPa gauge) AND
ELEVATED TEMPERATURES

| Temp. °C. | Impeller Type | weight percent HOCl in Exit | PCH | PDC | DCH | DCIPE | MCA |
|---|---|---|---|---|---|---|---|
| 50 | gas inducing | 0.08 | 97.16 | 1.07 | 0.80 | 0.86 | 0.11 |
| 60 | gas inducing | 0.01 | 97.75 | 0.89 | 0.57 | 0.76 | 0.04 |
| 60 | non-gas inducing | 0.55 | 95.65 | 1.36 | 1.06 | 0.66 | 1.25 |
| 70 | gas inducing | 0.003 | 97.61 | 0.97 | 0.42 | 0.98 | 0.03 |
| 80 | gas inducing | 0.00 | 96.17 | 1.94 | 0.91 | 0.86 | 0.13 |
| 80 | non-gas inducing | 0.01 | 95.23 | 2.00 | 1.25 | 0.92 | 0.60 |

Abbreviations are as for Table 3.

These data show that at elevated pressures, an improvement in PCH selectivity and a reduction in MCA selectivity are obtained for temperatures up to 80° C. As in Example 7, MCA and DCH selectivities are shown to be a function of the exit HOCl concentration. The data also show the advantage of the gas inducing impeller, especially at the lower temperatures where the reaction rates are slower. HOCl conversion and PCH selectivity are increased and MCA and DCH selectivities are reduced with the use of the gas inducing impeller.

COMPARATIVE SAMPLE C: HYPOCHLORINATION PLUG FLOW REACTOR USING CHLORINE

Water (140 ml/min) at 80° C., propylene gas (1600 ml/min, 3 g/min) at 25° C., and chlorine gas (1600 ml/min, 5.06 g/min) at 25° C. are continuously fed to a vertical coil plug flow (tubular) reactor (6.35 mm diameter by 6.8 m long) with feed in the bottom and product taken off the top of the coil reactor. The reactor is insulated to minimize heat losses. Pressure at the discharge of the reactor is atmospheric (101.3 kPa absolute) with an inlet pressure of about 5 psig (34.5 kPa gauge) and an estimated residence time of 45 seconds. Product exiting the plug flow reactor is collected in a liquid trap chilled to about 40° C. and analyzed by gas chromatography using a flame ionization detector. Average product molar selectivities based on the feed propylene are: 90.9 percent propylene chlorohydrin (PCH), 6.5 percent propylene dichloride (PDC), 0.1 percent trichloropropane (TCP), 0.9 percent dichlorohydrin (DCH), 1.5 percent dichloroisopropyl ether (DCIPE), and 0.1 percent monochloroacetone (MCA).

The data from Comparative Sample C and Example 7 considered together show the advantage of using a CSTR as compared with a plug flow reactor and gaseous chlorine for hypochlorination as in Comparative Sample C in the improved PCH selectivity and reduced PDC selectivity.

COMPARATIVE SAMPLE D: HYPOCHLORINATION WITH HOCl IN A PLUG FLOW REACTOR

A series of runs are made in which chlorine feed is replaced by hypochlorous acid solution feed with concentrations varying from 2.0–5.0 weight percent and fed at 70 ml/min to the reactor of Comparative Sample C modified to be 13.7 m long. Propylene gas (an amount stoichiometric with the HOCl) is continuously fed to the plug flow reactor along with the HOCl solution. Temperatures along the reactor vary from 60°–80° C. in each of the runs with the HOCl feed at 60° C. and the reactor outlet at 80° C. Product is captured and analyzed as in Comparative Sample C. The product contains 1400–2000 ppm chlorides. Table 5 shows average molar selectivities of the major products based on propylene:

TABLE 5

AVERAGE MOLE PERCENT SELECTIVITIES USING LOW-CHLORIDES HOCl SOLUTIONS REACTED WITH PROPYLENE IN A PLUG FLOW REACTOR

| weight percent HOCl in Feed | 5.0 percent HOCl | 3.6 percent HOCl | 2.7 percent HOCl | 2.0 percent HOCl |
|---|---|---|---|---|
| PCH | 93.2 | 94.5 | 95.0 | 94.6 |
| PDC | 2.2 | 2.1 | 2.3 | 2.4 |
| DCH | 0.8 | 0.9 | 0.8 | 1.2 |
| DCIPE | 2.2 | 1.2 | 0.7 | 0.5 |
| MCA | 1.6 | 1.4 | 1.2 | 1.3 |

Abbreviations are as for Table 3.

This Comparative Sample shows that the use of low-chlorides HOCl solutions in a plug flow reactor does reduce the selectivity of PDC formation, but unexpectedly increases the selectivity to the undesirable MCA.

The data from Comparative Samples C and D and Example 7 considered together show the advantage of using a backmix reactor with low chloride HOCl as compared with a plug flow reactor with either gaseous chlorine for hypochlorination as in Comparative Sample C (improved PHC selectivity and reduced PDC selectivity) or compared with using low-chlorides HOCl solution as in Comparative Sample D (reduced MCA selectivity).

EXAMPLE 10: REMOVAL OF CHLORATES BY ACID ADDITION

An acid/brine solution is prepared by mixing 202.83 g NaCl, 608.5 g water, and 87.47 g of 5N HCl. A sample, 429.12 g, of this solution is heated to 107° C. To the resulting mixture, is added 3.59 g of a 19.83 weight percent $NaClO_3$ in water solution. The chlorate ion concentration is measured by ion chromatography and its variation with time is shown in Table 6:

TABLE 6

CHLORATE REMOVAL

| Time, min. | mole/liter Chlorate |
|---|---|
| 0 | 0.014194 |
| 1 | 0.005297 |
| 2 | 0.003069 |
| 3 | 0.001472 |
| 4 | 0.000719 |
| 5 | none detected |

This data shows that chlorates can be removed from brine by the addition of hydrochloric acid by heating.

We claim:

1. A continuous process for preparing an olefin chlorohydrin comprising steps of:
   (a) contacting chlorine with a solution of a metal hypochlorite at a temperature below about 60° C., and a pH of less than about 5.5, with sufficient micromixing to achieve a product hypochlorous acid in a yield of at least about 80 mole percent based on hypochlorite in an aqueous metal chloride solution;
   (b) separating at least a portion of the hypochlorous acid from the aqueous metal chloride solution thereof wherein the solution is sprayed as droplets having a volume mean diameter of less than about 500 micrometers into a vapor stream such that at least about 30 mole percent of the hypochlorous acid is desorbed from a liquid phase into a vapor phase where hypochlorous acid and dichlorine monoxide are in equilibrium;
   (c) distilling the remaining liquid phase to obtain additional hypochlorous acid and dichlorine monoxide vapor;
   (d) absorbing the hypochlorous acid and dichlorine monoxide in low-chlorides water to produce a low-chlorides aqueous hypochlorous acid solution; and
   (e) contacting the low-chlorides aqueous hypochlorous acid solution with an olefin in a continuous process using a continuous stirred tank reactor with backmix stirring sufficient to maintain the HOCl concentration in the reactor of 0.2 weight percent or less to form a corresponding olefin chlorohydrin.

2. The process of claim 1 additionally comprising steps:
   (f) contacting the olefin chlorohydrin with a base to form a corresponding alkylene oxide and a salt solution; and
   (g) separating the alkylene oxide from the salt solution.

3. The process of claim 2 wherein the base in Step (f) is an alkali metal hydroxide, said process additionally comprising a step preceding Step (a) of contacting an alkaline earth metal hydroxide or oxide with chlorine to form an alkaline earth metal hypochlorite solution.

4. The process of claim 3 wherein the alkaline earth metal hydroxide or oxide is calcium hydroxide or oxide.

5. The process of claim 3 wherein the alkaline earth hypochlorite solution is fed to Step (a) at a temperature of from about 10° C. to about 60° C.

6. The process of claim 1 wherein chlorate ion produced in Step (a) is treated with acid to produce chlorine.

7. The process of claim 6 wherein the acid is hydrochloric acid.

8. The process of claim 6 wherein the chlorine is recycled to form hypochlorite used in Step (a) or to Step (a) or Step (c) or a combination thereof.

9. The process of claim 1 wherein the solution of a metal hypochlorite is at a temperature of from about 20° to about 45° C.

10. The process of claim 1 wherein micromixing in Step (a) is achieved in a backmixing reactor wherein shear is achieved by utilizing an impeller, baffles or a combination thereof.

11. The process of claim 10 wherein there is liquid recycle means from the reactor and residence time of less than about 200 seconds.

12. The process of claim 1 wherein the chlorine used in step (a) is liquid.

13. The process of claim 12 wherein reaction temperature in step (a) is from about 20° C. to about 45° C.

14. The process of claim 12 wherein the pH in step (a) is from about 2.5 to about 4.5.

15. The process of claim 14 wherein the droplets of step (b) have a volume mean diameter less than about 200 micrometers.

16. The process of claim 15 wherein the droplets of step (b) have a volume mean diameter of from about 25 to about 200 micrometers.

17. The process of claim 16 wherein the droplets have a volume mean diameter of from about 40 to about 200 micrometers.

18. The process of claim 14 wherein, in step (b) the droplets are produced by an atomizing means which is a single phase liquid spray nozzle.

19. The process of claim 14 wherein, in step (b) the droplets are produced by an atomizing means which is a two phase liquid spray nozzle.

20. The process of claim 19 wherein in step (b) from about 30 to about 70 mole percent of the hypochlorous acid formed in step (a) is desorbed from the liquid phase into a vapor phase.

21. The process of claim 1 wherein step (b) and step (c) take place at a pressure of from about 20 to about 133 kPa.

22. The process of claim 1 wherein step (b) and step (c) take place at a temperature of from about 40° C. to about 100° C.

23. The process of claim 1 wherein step (b) and step (c) take place at a temperature of from about 50° C. to about 80° C.

24. The process of claim 1 wherein step (c) takes place in a packed distillation column having sufficient packing to be equivalent to at least one theoretical transfer unit.

25. The process of claim 1 wherein gases are collected from step (d) and are recycled to step (c).

26. The process of claim 1 wherein in step (c), there is a stripping gas comprising chlorine, steam or a combination thereof.

27. The process of claim 26 wherein the stripping gas is chlorine.

28. The process of claim 26 wherein the stripping gas is steam.

29. The process of claim 26 wherein the stripping gas is introduced below packing in a column.

30. The process of claim 1 wherein the low-chlorides aqueous hypochlorous acid solution has a concentration of from about 3 to about 7 weight percent hypochlorous acid.

31. The process of claim 30 wherein the concentration is from about 4 to about 5 weight percent.

32. The process of claim 31 wherein the solution contains less than about 500 parts per million by weight chloride ion.

33. The process of claim 32 wherein the solution contains less than about 200 parts per million by weight chloride ion.

34. The process of claim 1 wherein step (d) takes place at a temperature of about 10° C. to about 60° C.

35. The process of claim 1 wherein step (d) takes place at a temperature of about 30° C. to about 60° C.

36. The process of claim 1 wherein the olefin is selected from propylene, 1-butene, 3 chloropropene, ethylene and mixtures thereof.

37. The process of claim 36 wherein the olefin is propylene.

38. The process of claim 37 wherein step (e) takes place at a temperature of from about 60° C. to about 90° C.

39. The process of claim 38 wherein step (e) takes place at a temperature of from about 60° C. to about 80° C.

40. The process of claim 1 wherein, in step (e), a gas inducing contactor is used for agitation and gas is introduced below the contactor.

41. The process of claim 1 wherein step (e) has a reaction time of less than about 30 minutes.

42. The process of claim 1 wherein in step (e) the pressure is from about 0 to about 415 kPa gauge, and the concentration of chlorohydrin produced is from about 5 to about 10 weight percent in water.

43. The process of claim 42 wherein in step (e) takes place at a temperature of at least about 60° C.

44. The process of claim 43 wherein step (e) takes place at a pressure greater than about one atmosphere (101.3 kPa), less than about 30 minutes reaction time, HOCl feed concentration is less than about 7 weight percent, and there is internal gas recycle.

45. A process for the manufacture of hypochlorous acid comprising a step of contacting chlorine and a solution of a metal hypochlorite having a hypochlorite concentration of at least about 1M at a temperature below about 60° C., and a pH of less than about 5.5, with sufficient micromixing to achieve a product hypochlorous acid in a yield of at least about 80 mole percent based on hypochlorite.

46. The process of claim 45 wherein the chlorine is liquid.

47. A process for the manufacture of hypochlorous acid comprising a step of separating at least a portion the hypochlorous acid from an aqueous metal chloride solution thereof, wherein the solution is sprayed as droplets having a volume mean diameter of less than about 500 micrometers into a vapor stream such that at least about 30 mole percent of the hypochlorous acid is rapidly desorbed from the liquid into the vapor phase with hypochlorous acid being in the vapor phase as hypochlorous acid and dichlorine monoxide.

48. The process of claim 47 wherein after spraying the liquid falls into a distillation zone.

49. The process of claim 48 wherein the distillation zone contains trays or packing.

50. A continuous process of preparing an olefin chlorohydrin comprising a step of contacting a low-chlorides aqueous hypochlorous acid solution with an olefin in a continuous stirred tank reactor at a temperature of at least about 60° C., pressure greater than about one atmosphere (101.3 kPa), less than 30 minutes residence time, HOCl feed concentration less than about 7 weight percent, with internal gas recycle and backmix stirring sufficient to maintain the HOCl concentration in the reactor of 0.2 weight percent or less to form a corresponding olefin chlorohydrin.

51. The process of claim 50 wherein there is recycle of olefin which escapes from the solution back into the solution.

52. The process of claim 51 wherein the recycle is accomplished internal to a reaction vessel containing the solution.

53. The process of claim 52 wherein the recycle is accomplished by using a gas inducing contactor.

54. The process of claim 53 wherein the gas inducing contactor is a gas inducing impeller, or helical screw with in a draft tube.

* * * * *